(12) United States Patent
Lippert et al.

(10) Patent No.: US 9,067,333 B2
(45) Date of Patent: Jun. 30, 2015

(54) MICRO-FABRICATED GUIDEWIRE DEVICES HAVING ELASTOMERIC FILL COMPOSITIONS

(75) Inventors: John Lippert, Incline Village, NV (US); Edward J. Snyder, Park City, UT (US)

(73) Assignee: Scientia Vascular, LLC, Incline Village, NV (US)

( * ) Notice: Subject to any disclaimer, the term of this patent is extended or adjusted under 35 U.S.C. 154(b) by 534 days.

(21) Appl. No.: 12/753,842

(22) Filed: Apr. 2, 2010

(65) Prior Publication Data

US 2010/0256606 A1     Oct. 7, 2010

Related U.S. Application Data

(63) Continuation-in-part of application No. 12/633,727, filed on Dec. 8, 2009, now Pat. No. 8,468,919.

(60) Provisional application No. 61/166,480, filed on Apr. 3, 2009.

(51) Int. Cl.
| | |
|---|---|
| *A61M 25/00* | (2006.01) |
| *B26F 1/00* | (2006.01) |
| *A61M 25/09* | (2006.01) |
| *B26D 5/20* | (2006.01) |

(52) U.S. Cl.
CPC .......... *B26F 1/0061* (2013.01); *A61M 25/0009* (2013.01); *A61M 25/0051* (2013.01); *A61M 25/0053* (2013.01); *A61M 25/09* (2013.01); *A61M 2025/0042* (2013.01); *A61M 2025/09108* (2013.01); *A61M 2025/09133* (2013.01); *B26D 5/20* (2013.01); *B26F 1/0053* (2013.01)

(58) Field of Classification Search
CPC ............... A61M 25/09; A61M 2025/09083; A61M 2025/09133; A61M 2025/09175
USPC .......................................... 600/585; 604/529
See application file for complete search history.

(56) References Cited

U.S. PATENT DOCUMENTS

| | | |
|---|---|---|
| 3,572,334 A | 3/1971 | Petterson |
| 3,612,058 A | 10/1971 | Ackerman |
| 3,920,058 A | 11/1975 | Walker |
| 4,163,406 A | 8/1979 | Crawford |

(Continued)

FOREIGN PATENT DOCUMENTS

| | | |
|---|---|---|
| CN | 1230914 | 10/1999 |
| CN | 1324285 | 11/2001 |

(Continued)

OTHER PUBLICATIONS

U.S. Appl. No. 12/753,831, Feb. 1, 2012, Office Action.

(Continued)

*Primary Examiner* — Max Hindenburg
(74) *Attorney, Agent, or Firm* — Workman Nydegger

(57) ABSTRACT

A guidewire device comprising a micro-fabricated elongated outer member having an outer surface and an interior surface forming a lumen extending from a proximal end to a distal end and a plurality of fenestrations made through said outer surface and said interior surface into a least a portion of said lumen; an outer elastomer laminate layer in contact with at least a portion of said outer surface and filling at least a portion of said plurality of fenestrations; and an inner member disposed within a substantial portion of said lumen, and embodiments thereof.

17 Claims, 19 Drawing Sheets

CATHETER WITH PROXIMAL CUTS FOR KINK RESISTANCE, AND SHAPE HOLDING TIP.

(56) References Cited

U.S. PATENT DOCUMENTS

| | | | |
|---|---|---|---|
| 4,239,069 A | 12/1980 | Zimmerman | |
| 4,416,312 A | 11/1983 | Ostberg | |
| 4,719,924 A | 1/1988 | Crittenden et al. | |
| 4,846,186 A | 7/1989 | Box et al. | |
| 4,895,168 A | 1/1990 | Machek | |
| 4,989,608 A | 2/1991 | Ratner | |
| 5,047,045 A | 9/1991 | Arney et al. | |
| 5,084,022 A | 1/1992 | Claude | |
| 5,095,915 A | 3/1992 | Engelson | |
| 5,154,725 A | 10/1992 | Leopold | |
| 5,315,996 A | 5/1994 | Lundquist | |
| 5,372,587 A | 12/1994 | Hammerslag et al. | |
| 5,385,152 A | 1/1995 | Abele et al. | |
| 5,437,288 A | 8/1995 | Schwartz et al. | |
| 5,506,682 A | 4/1996 | Pryor | |
| 5,507,751 A | 4/1996 | Goode et al. | |
| 5,573,520 A | 11/1996 | Schwartz | |
| 5,673,707 A | 10/1997 | Chandrasekaran | |
| 5,676,659 A | 10/1997 | McGurk | |
| 5,690,120 A | 11/1997 | Jacobsen et al. | |
| 5,741,429 A | 4/1998 | Donadio | |
| 5,746,701 A | 5/1998 | Noone | |
| 5,800,454 A | 9/1998 | Jacobsen et al. | |
| 5,833,632 A | 11/1998 | Jacobsen et al. | |
| 5,860,963 A | 1/1999 | Azam | |
| 5,911,715 A | 6/1999 | Berg | |
| 5,911,717 A | 6/1999 | Jacobsen et al. | |
| 5,916,194 A | 6/1999 | Jacobsen et al. | |
| 5,931,830 A | 8/1999 | Jacobsen et al. | |
| 6,004,279 A * | 12/1999 | Crowley et al. | 600/585 |
| 6,014,919 A | 1/2000 | Jacobsen et al. | |
| 6,017,319 A | 1/2000 | Jacobsen et al. | |
| 6,022,343 A | 2/2000 | Johnson et al. | |
| 6,022,369 A | 2/2000 | Jacobsen et al. | |
| 6,027,863 A | 2/2000 | Donadis | |
| 6,033,288 A | 3/2000 | Weisshaus et al. | |
| 6,033,394 A | 3/2000 | Vidlund | |
| 6,063,101 A | 5/2000 | Jacobsen et al. | |
| 6,132,389 A | 10/2000 | Cornish | |
| 6,139,511 A | 10/2000 | Huter | |
| 6,179,828 B1 | 1/2001 | Mottola et al. | |
| 6,183,410 B1 | 2/2001 | Jacobsen et al. | |
| 6,214,042 B1 | 4/2001 | Jacobsen et al. | |
| 6,228,073 B1 | 5/2001 | Noone | |
| 6,260,458 B1 | 7/2001 | Jacobsen et al. | |
| 6,261,246 B1 | 7/2001 | Pantages et al. | |
| 6,302,870 B1 | 10/2001 | Jacobsen et al. | |
| 6,346,091 B1 | 2/2002 | Jacobsen et al. | |
| 6,356,791 B1 | 3/2002 | Westlund et al. | |
| 6,402,706 B2 | 6/2002 | Richardson et al. | |
| 6,428,489 B1 | 8/2002 | Jacobsen et al. | |
| 6,431,039 B1 | 8/2002 | Jacobsen et al. | |
| 6,436,056 B1 | 8/2002 | Wang et al. | |
| 6,440,088 B1 | 8/2002 | Jacobsen et al. | |
| 6,464,651 B1 | 10/2002 | Hiejima et al. | |
| 6,527,746 B1 | 3/2003 | Oslund et al. | |
| 6,553,880 B2 | 4/2003 | Jacobsen et al. | |
| 6,554,820 B1 | 4/2003 | Chin et al. | |
| 6,558,355 B1 | 5/2003 | Metzger | |
| 6,610,046 B1 | 8/2003 | Usami et al. | |
| 6,671,560 B2 | 12/2003 | Westlund et al. | |
| 6,766,720 B1 | 7/2004 | Jacobsen et al. | |
| RE39,018 E | 3/2006 | Azuma | |
| 7,110,910 B1 | 9/2006 | Deffenbaugh et al. | |
| 7,494,474 B2 | 2/2009 | Richardson et al. | |
| 5,685,868 A1 | 11/2009 | Lundquist | |
| 7,621,880 B2 | 11/2009 | Ryan | |
| 7,766,896 B2 | 8/2010 | Volk | |
| 7,989,042 B2 | 8/2011 | Obara et al. | |
| 8,043,314 B2 | 10/2011 | Noriega et al. | |
| 8,048,004 B2 | 11/2011 | Davis et al. | |
| 8,915,865 B2 | 12/2014 | Jacobsen et al. | |
| 2002/0019599 A1 * | 2/2002 | Rooney et al. | 600/585 |
| 2003/0023190 A1 * | 1/2003 | Cox | 600/585 |
| 2003/0093059 A1 * | 5/2003 | Griffin et al. | 604/525 |
| 2004/0054349 A1 | 3/2004 | Brightbill | |
| 2004/0087933 A1 | 5/2004 | Lee | |
| 2004/0102719 A1 | 5/2004 | Keith et al. | |
| 2004/0181174 A2 * | 9/2004 | Davis et al. | 600/585 |
| 2004/0193140 A1 | 9/2004 | Griffin | |
| 2005/0054953 A1 | 3/2005 | Ryan | |
| 2005/0124976 A1 * | 6/2005 | Devens et al. | 604/523 |
| 2006/0112802 A1 | 6/2006 | Fujinami | |
| 2007/0010786 A1 | 1/2007 | Casey et al. | |
| 2007/0100285 A1 | 5/2007 | Griffin et al. | |
| 2007/0112331 A1 | 5/2007 | Weber et al. | |
| 2007/0135763 A1 | 6/2007 | Musbach | |
| 2007/0167876 A1 | 7/2007 | Euteneuer et al. | |
| 2007/0250036 A1 | 10/2007 | Volk | |
| 2007/0287955 A1 | 12/2007 | Layman et al. | |
| 2008/0021347 A1 | 1/2008 | Jacobsen et al. | |
| 2008/0021404 A1 | 1/2008 | Jacobsen et al. | |
| 2008/0064989 A1 | 3/2008 | Chen et al. | |
| 2008/0077049 A1 | 3/2008 | Hirshman | |
| 2008/0097247 A1 | 4/2008 | Eskuri | |
| 2008/0097248 A1 | 4/2008 | Munoz et al. | |
| 2008/0125674 A1 | 5/2008 | Bilecen et al. | |
| 2008/0147170 A1 | 6/2008 | Vrba | |
| 2008/0188928 A1 | 8/2008 | Salahieh | |
| 2008/0200839 A1 | 8/2008 | Bunch et al. | |
| 2008/0269641 A1 | 10/2008 | O'Shaughnessy et al. | |
| 2009/0043283 A1 | 2/2009 | Turnlund et al. | |
| 2009/0177119 A1 * | 7/2009 | Heidner et al. | 600/585 |
| 2010/0063479 A1 | 3/2010 | Merddan | |
| 2010/0139465 A1 | 6/2010 | Christian | |
| 2010/0256527 A1 | 10/2010 | Lippert | |
| 2010/0256528 A1 | 10/2010 | Lippert | |
| 2010/0256601 A1 | 10/2010 | Lippert | |
| 2010/0256602 A1 | 10/2010 | Lippert | |
| 2010/0256603 A1 | 10/2010 | Lippert | |
| 2010/0256604 A1 | 10/2010 | Lippert | |
| 2010/0256605 A1 | 10/2010 | Lippert | |
| 2013/0255456 A1 | 10/2013 | Christian | |

FOREIGN PATENT DOCUMENTS

| | | |
|---|---|---|
| CN | 1518428 | 8/2004 |
| CN | 1781684 | 6/2006 |
| JP | 07-008560 | 1/1995 |
| JP | 08-308934 | 11/1996 |
| JP | 11294497 | 10/1999 |
| JP | 2000-116787 | 4/2000 |
| JP | 2002543896 | 12/2002 |
| JP | 2003011117 | 1/2003 |
| JP | 2004329552 | 11/2004 |
| JP | 2005533594 | 11/2005 |
| JP | 2007313638 | 12/2007 |
| JP | 2008536639 | 9/2008 |
| WO | 2004071076 | 2/2004 |
| WO | WO2006/113863 | 10/2006 |
| WO | 2009020961 | 2/2009 |
| WO | 2009020962 | 2/2009 |
| WO | 2010077692 | 7/2010 |
| WO | 2010115163 | 10/2010 |

OTHER PUBLICATIONS

U.S. Appl. No. 12/753,831, May 31, 2012, Final Office Action.
U.S. Appl. No. 12/753,836, Feb. 1, 2012, Office Action.
U.S. Appl. No. 12/753,836, May 31, 2012, Final Office Action.
U.S. Appl. No. 12/753,839, Feb. 7, 2012, Office Action.
U.S. Appl. No. 12/753,839, May 31, 2012, Final Office Action.
U.S. Appl. No. 12/753,855, Sep. 15, 2011, Office Action.
U.S. Appl. No. 12/753,855, Apr. 18, 2012, Final Office Action.
U.S. Appl. No. 12/753,858, May 10, 2011, Office Action.
U.S. Appl. No. 12/753,858, Oct. 19, 2011, Final Office Action.
U.S. Appl. No. 12/753,858, Feb. 3, 2012, Office Action.
U.S. Appl. No. 12/753,858, Jul. 18, 2012, Final Office Action.
U.S. Appl. No. 12/753,849, May 10, 2011, Office Action.
U.S. Appl. No. 12/753,849, Oct. 18, 2011, Office Action.
U.S. Appl. No. 12/753,849, Jun. 6, 2012, Final Office Action.
U.S. Appl. No. 12/633,727, Oct. 16, 2012, Office Action.
EP10759515.9 Supplemntary European Search Report dated Sep. 25, 2012.

(56) References Cited

OTHER PUBLICATIONS

U.S. Appl. No. 12/753,849, May 27, 2014, Office Action.
U.S. Appl. No. 12/753,831, Mar. 21, 2014, Office Action.
U.S. Appl. No. 12/633,727, Feb. 28, 2013, Notice of Allowance.
U.S. Appl. No. 12/753,849, Oct. 9, 2013, Final Office Action.
U.S. Appl. No. 12/753,858, Jan. 17, 2014, Final Office Action.
U.S. Appl. No. 12/753,855, Feb. 28, 2014, Office Action.
U.S. Appl. No. 12/753,849, Jan. 3, 2013, Office Action.
U.S. Appl. No. 12/753,858, Mar. 29, 2013, Office Action.
U.S. Appl. No. 12/753,839, May 5, 2014, Office Action.
U.S. Appl. No. 12/753,836, Jul. 31, 2014, Office Action.
U.S. Appl. No. 12/753,831, Aug. 29, 2014, Final Office Action.
U.S. Appl. No. 12/753,858, Sep. 4, 2014, Office Action.
International Search Report for PCT/US2009/067217 dated Dec. 16, 2010.
International Search Report for PCT/US2010/029867 dated Jun. 1, 2010.
European Search Report for EP09836735 dated Nov. 7, 2012.
U.S. Appl. No. 12/753,858, mailed Nov. 4, 2014, Interview Summary.
U.S. Appl. No. 12/753,836, mailed Jan. 9, 2015, Final Office Action.
U.S. Appl. No. 12/753,849, mailed Dec. 5, 2014, Interview Summary.
U.S. Appl. No. 12/753,855, mailed Jan. 13, 2015, Final Office Action.
U.S. Appl. No. 12/753,849, mailed Feb. 2, 2015, Notice of Allowance.
U.S. Appl. No. 12/753,831, mailed Apr. 14, 2015, Notice of Allowance
U.S. Appl. No. 12/753,849, mailed Apr. 30, 2015, Notice of Allowance.
U.S. Appl. No. 12/753,855, mailed May 21, 2015, Office Action.

\* cited by examiner

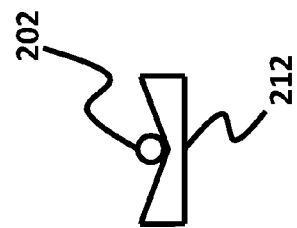
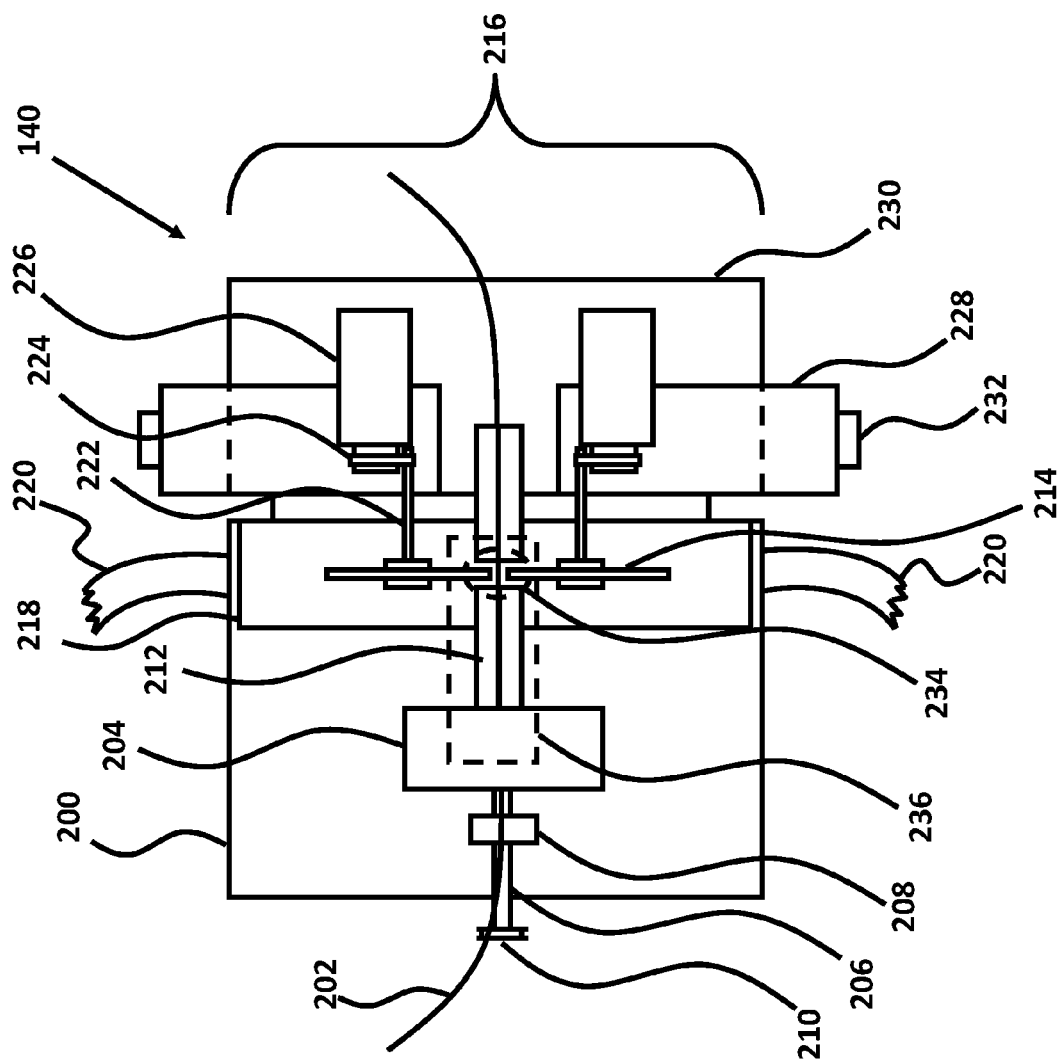

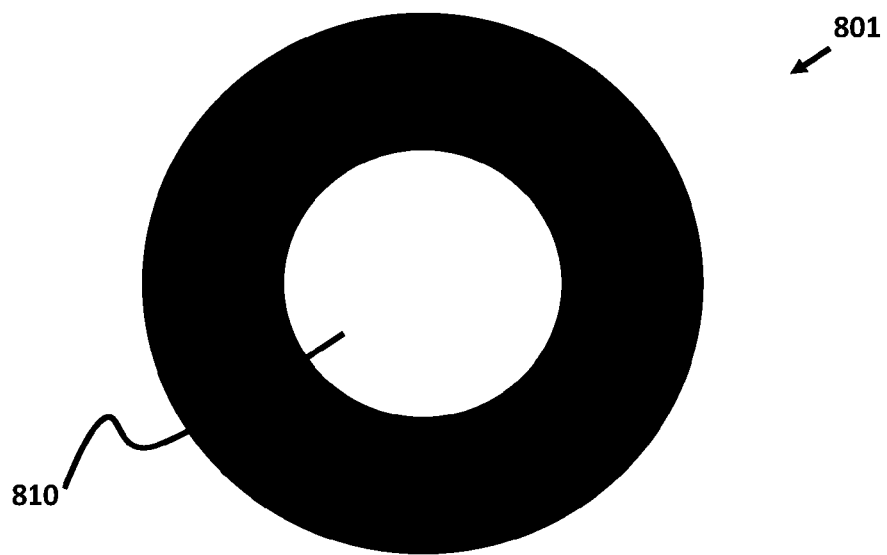
PRIOR ART   FIG. 8A
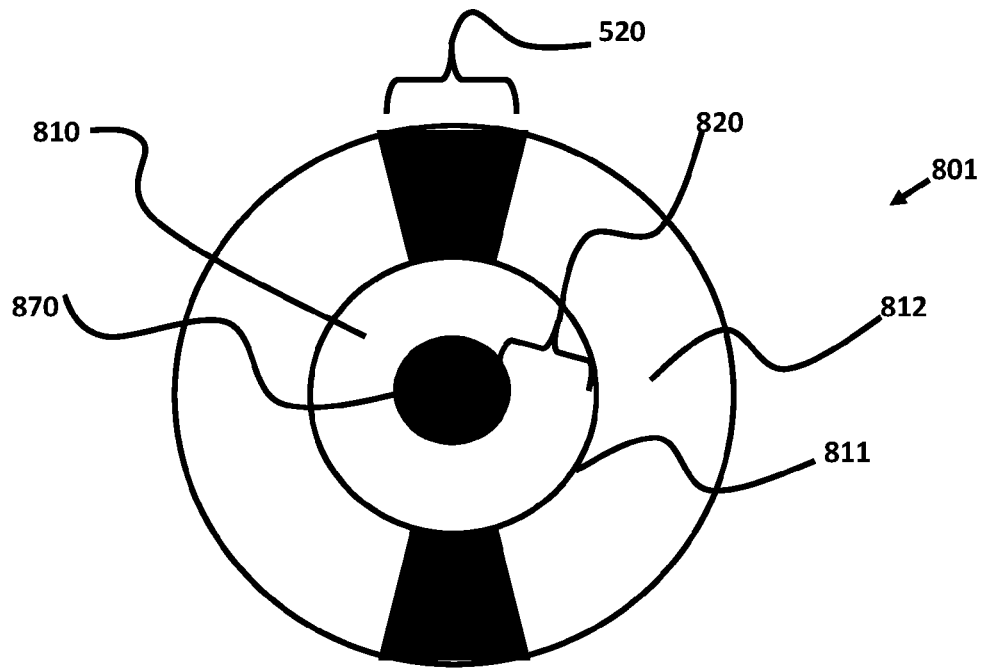
PRIOR ART   FIG. 8B

CATHETER WITH SS PROXIMAL, MICRO-FABRICATED DISTAL AND ELASTOMER FILLING, INNER LINER, DISTAL TIP, AND HUB, AND DISTAL DIAM GREATER THAN PROXIMAL DIAM.

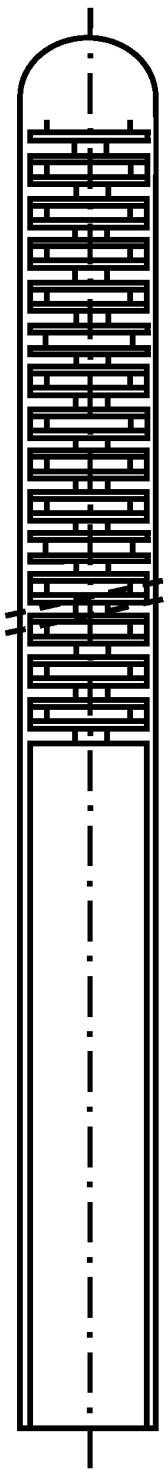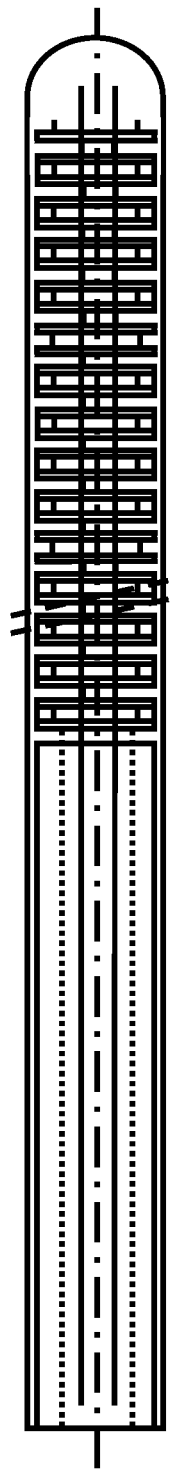
FIG. 14B SOLID WIRE GUIDEWIRE WITH INTERSPERCED ELASTOMER FILLING
FIG. 14C HOLLOW TUBE GUIDEWIRE WITH CORE WIRE AND INTERSPERCED ELASTOMER FILLING

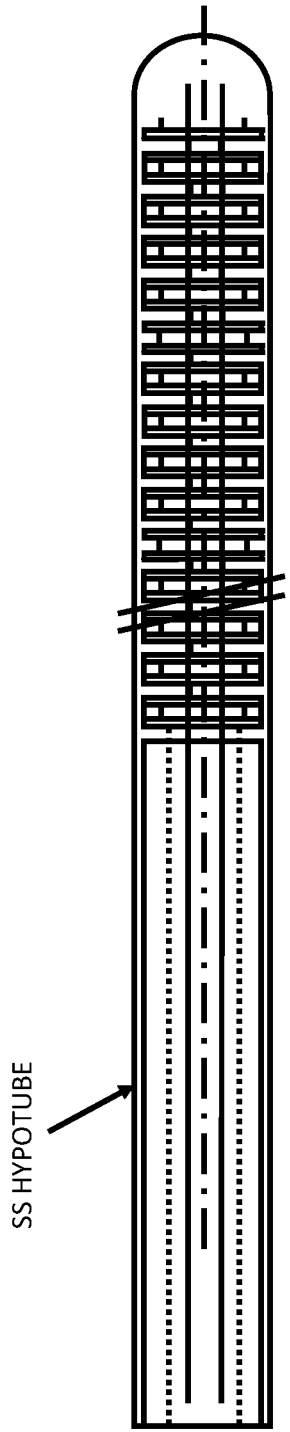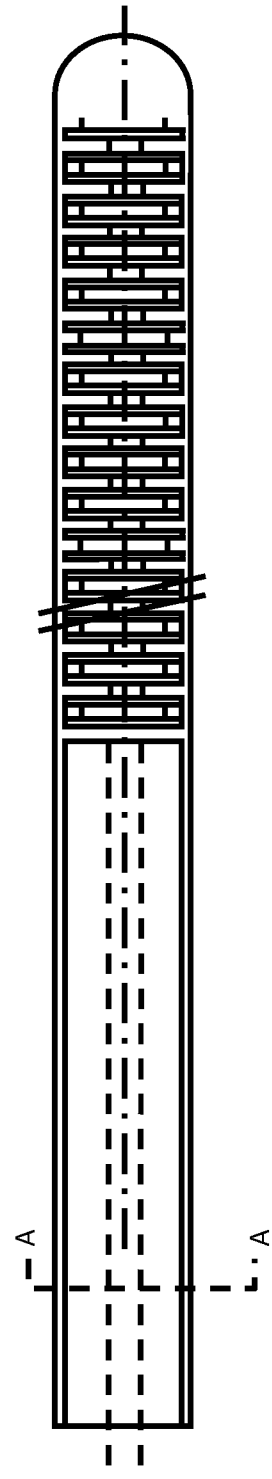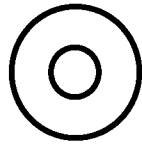
HOLLOW TUBE GUIDEWIRE WITH CORE WIRE AND INTERSPERCED ELASTOMER FILLING AND HYPOTUBE PROXIMAL.
HOLLOW TUBE GUIDEWIRE WITH CORE WIRE AND INTERSPERCED ELASTOMER FILLING AND HYPOTUBE PROXIMAL.
SS HYPOTUBE
SECTION AA PEEK EXTRUDED OVER WIRE
FIG. 14D

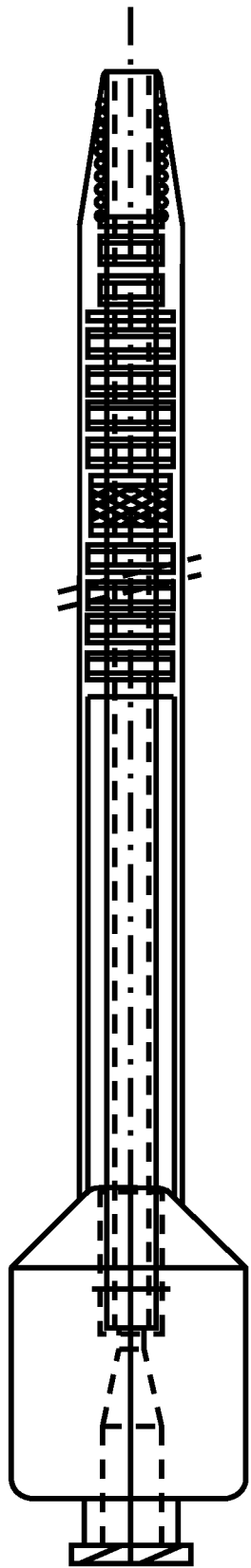
CATHETER WITH FULL LENGTH TUBULAR SHAFT, MICRO-FABRICATED DISTAL AND ELASTOMER FILLING, INNER LINER, DISTAL TIP, AND HUB.
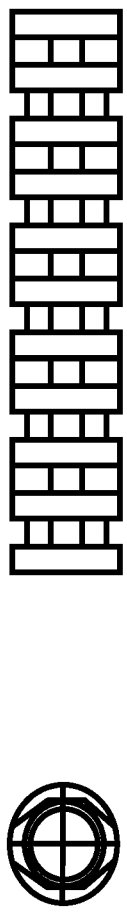
MICRO-FABRICATED CATHETER SHAFT WITH CUTS THAT DO NOT CUT THROUGH TO THE LUMEN.
FIG. 15A

CATHETER WITH PROXIMAL CUTS FOR KINK RESISTANCE, AND SHAPE HOLDING TIP.

MICRO-FABRICATED GUIDEWIRE DEVICES HAVING ELASTOMERIC FILL COMPOSITIONS

CROSS-REFERENCES TO RELATED APPLICATIONS

This non-provisional application takes priority to provisional application Ser. No. 61/166,480, filed 3 Apr. 2009 and is a continuation-in-part application of non-provisional application Ser. No. 12/633,727, filed 8 Dec. 2009. Both applications are hereby incorporated in their entirety by reference.

BRIEF DESCRIPTION OF THE INVENTION

An embodiment of the invention is generally related to polymer catheters and guidewires for use in intravascular surgery, and more particularly related to various embodiments of polymer catheters and guidewires micro-machined with a micro-cutting machine to provide sufficient flexibility to travel through a patient's vasculature while retaining sufficient torquability to transmit torque from a proximal end to the distal end of the catheter or guidewire, and methods of producing the same.

An embodiment of the invention is generally related to hybrid catheters and guidewires for use in intravascular surgery, and more particularly related to various embodiments of hybrid catheters and guidewires micro-machined from two or more stock materials with a micro-cutting machine to provide sufficient flexibility to travel through a patient's vasculature while retaining sufficient torquability to transmit torque from a proximal end to the distal end of the catheter or guidewire, and methods of producing the same.

An embodiment of the invention is generally related to catheters for transporting relatively high pressure fluids through a patient's vasculature, and more particularly related to catheters micro-machined so as to avoid penetrating a lumen wall of the catheter so as to preserve the fluid pressure integrity of the catheter without inclusion of a flexibility hindering liner tube, and methods of producing the same.

An embodiment of the invention is generally related to stabilizing the torque transmission of a micro-cut catheter or guidewire while the catheter or guidewire is under flexing strain, and more particularly related to utilizing elastomer laminate to stabilize the micro-machined structure so as to avoid deformation while under flexing strain and thereby reliably transmit torque to a distal end of the catheter or guidewire.

An embodiment of the invention is generally related to catheters for transporting relatively high pressure fluids through a patient's vasculature, and more particularly related to an apparatus for and methods of utilizing an elastomer laminate to fill fenestrations in a micro-machined skeletal structure, thereby re-establishing fluid pressure integrity of the catheter's lumen without use of a flexibility hindering liner tube.

An embodiment of the invention is generally related to hybrid laminated catheters and guidewires for use in intravascular surgery, and more particularly related to a soft tip configuration for use with various embodiments of catheters and guidewires to provide a gradual stiffness transitioning towards the distal end of the catheter or guidewire and to provide a shapeable tip that a surgeon may custom bend to fit a particular procedure or a particular patient's vasculature.

An embodiment of the invention is generally related to guiding catheters for carrying large volumes of high pressure fluid deep into a patient's vasculature, and more particularly related to a micro-cut polymer guiding catheters with a shapeable soft tip that is sufficiently flexible to travel through a patient's carotid siphon while also retaining sufficient torquability to smoothly and reliably transmit torque through the entire length of the catheter.

An embodiment of the invention is generally related to a hybrid catheter having an outer diameter at its distal end that is larger than the outer diameter at its proximal end.

An embodiment of the invention is a torqueable hub having a barrel-shaped body with a plurality of longitudinal groves formed therein. The hub includes an axial interior space within which a syringe can be inserted.

STATEMENTS AS TO THE RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

The medical field utilizes highly flexible and torquable catheters and guidewires to perform delicate procedures deep inside the human body. Endovascular procedures typically start at the groin where a catheter and guidewire are inserted into the femoral artery and navigated up to the heart, brain, or other anatomy as required. Once in place, the guidewire is removed so the catheter can be used for the delivery of drugs, stents, embolic devices to treat a variety of conditions, or other devices or agents. The catheter may be a balloon catheter used for therapy directly, either by itself or with a balloon expandable stent pre-loaded on it. A radiopaque dye is often injected into the catheter so that the vessels can be viewed intraprocedurally or in the case of a diagnostic procedure, the dye may be the primary or only agent delivered through the catheter.

Intravascular procedures, by definition, work in and with delicate anatomy, namely the vessels themselves, which are often also compromised by disease. Damage to the vessels is particularly critical to avoid. If blood in the vessels is allowed to "leak," direct damage can be caused to any tissue outside of the normal capillary approach contacted by the blood, and/or may result in a deadly problem of exsanguination or "bleed out". When treating an aneurysm, the control of the catheter tip is especially important. An aneurysm is a very fragile ballooned vessel wall which can easily be punctured if the guidewire or catheter is not precisely controlled.

The guidewires and catheters produced with current technology machines (as described in published patents) have limited functionality. An example of such a micro-cutting machine is disclosed in U.S. Pat. No. 6,014,919, issued to Jacobsen et al. on 18 Jan. 2000. Due to the single blade design and other aspects of these existing machines, the machines lack the precision necessary to control small (sub 0.002") features on a reliable basis. They also lack the ability to precisely control and verify larger features, which could affect the safety and/or performance of these devices. These machines are also only capable of working with electrically conductive stock material because the machines rely on the electrical conductivity of the stock material to determine the position of the stock relative to the cutting blade. Each cut made by the blade into the stock is based on the location of the electrically sensed surface of the stock and the pre-programmed depth of the desired cut. Once a cut is made, the stock piece is rotated 180 degrees, the surface is sensed again, and another pre-programmed cut is made to a desired depth. As the cutting machine is incapable of determining the precise diameter (at the location of the cut) of the stock material being cut, each cut is made according to a preprogrammed depth regardless of that diameter. This is a problem because stock material is not always of a uniform shape and diameter—there are often imperfections along the length of stock that can affect both the roundness of the stock material and the diameter of the stock material at any particular location.

When the stock material is cut in the manner practiced by current cutting machines, a small beam of remaining material, of varying thickness, is formed by the sequential, opposing cuts. This beam is referred to as a resultant beam. If the diameter of the stock is thicker than anticipated at the location of the cuts, then the resultant beam will be thicker and therefore less flexible than desired. If the diameter of the stock is thinner than anticipated at the location of the cuts, then the resultant beam will be thinner and therefore weaker than desired. Thus, the critical dimension that governs both strength (safety) and flexibility (performance) is the width of the resultant beam, which in current micro-cutting machines is not controlled directly and is instead the result of two imprecise measurements—the measure of the relative distance between the blade and the stock material for the first cut and the measure of the relative distance between the blade and the stock material for the second cut. Any imperfection in the surface of the stock material, or inconsistency in the diameter of such material, is directly translated to the resultant beam. This is problematic in terms of both safety and performance of the final product, whether it is a guidewire, catheter or other device. It is especially critical when forming small dimension resultant beams relative to a larger dimension stock material, as an acceptable tolerance relative to the larger diameter of the stock material may be unacceptably large compared to the smaller dimension of the resultant beam. Existing technology is also unable to cut any kind of non-conductive material, such as plastic. The existing cutting machines rely upon electrical conductivity to sense the surface of the material being cut and then make the cuts.

It would therefore be advantageous to create a micro-cutting machine for machining catheters, guidewires and other devices that utilizes two blades to cut both sides simultaneously, that is able to directly control the width of resultant beams, and that is capable of micro-cutting non-conductive material, such as plastic. Such a machine would be faster, more predictable, and more versatile than current micro-cutting machines.

BRIEF DESCRIPTION OF THE SEVERAL VIEWS OF THE DRAWING

FIG. 3A illustrates a partially cut-away, plan view of a cutting assembly of the micro-cutting machine of FIG. 2 in an embodiment;

FIG. 3B illustrates a cross-sectional view of a piece of cylindrical stock material resting within a feed trough of the cutting assembly of FIG. 3A in an embodiment;

FIGS. 7A, 7B and 7C illustrate cross-sectional views across and along the length of pieces of cylindrical stock material cut to form different products, while

FIGS. 8A and 8B illustrate a prior art lumen forming stock material and a prior art resultant beam cut into a lumen forming stock material;

FIG. 14B illustrates a guidewire device in accordance with one or more embodiments.

FIG. 14C illustrates a guidewire device in accordance with one or more embodiments.

FIG. 14D illustrates a guidewire device in accordance with one or more embodiments.

FIG. 15A illustrates a catheter device in accordance with one or more embodiments.

DETAILED DESCRIPTION OF THE INVENTION

The herein disclosed embodiments of catheters and guidewires utilize previously unavailable combinations of materials and configurations to achieve superior levels of performance during surgical procedures. Several variations of micro-catheters, guiding catheters, and guidewires are described herein, as well as more general techniques that can improve the performance of any of these types of medical devices. A micro-cutting machine utilized to precisely cut cylindrical stock material used to form the catheters and guidewires is also disclosed.

Figure 1:
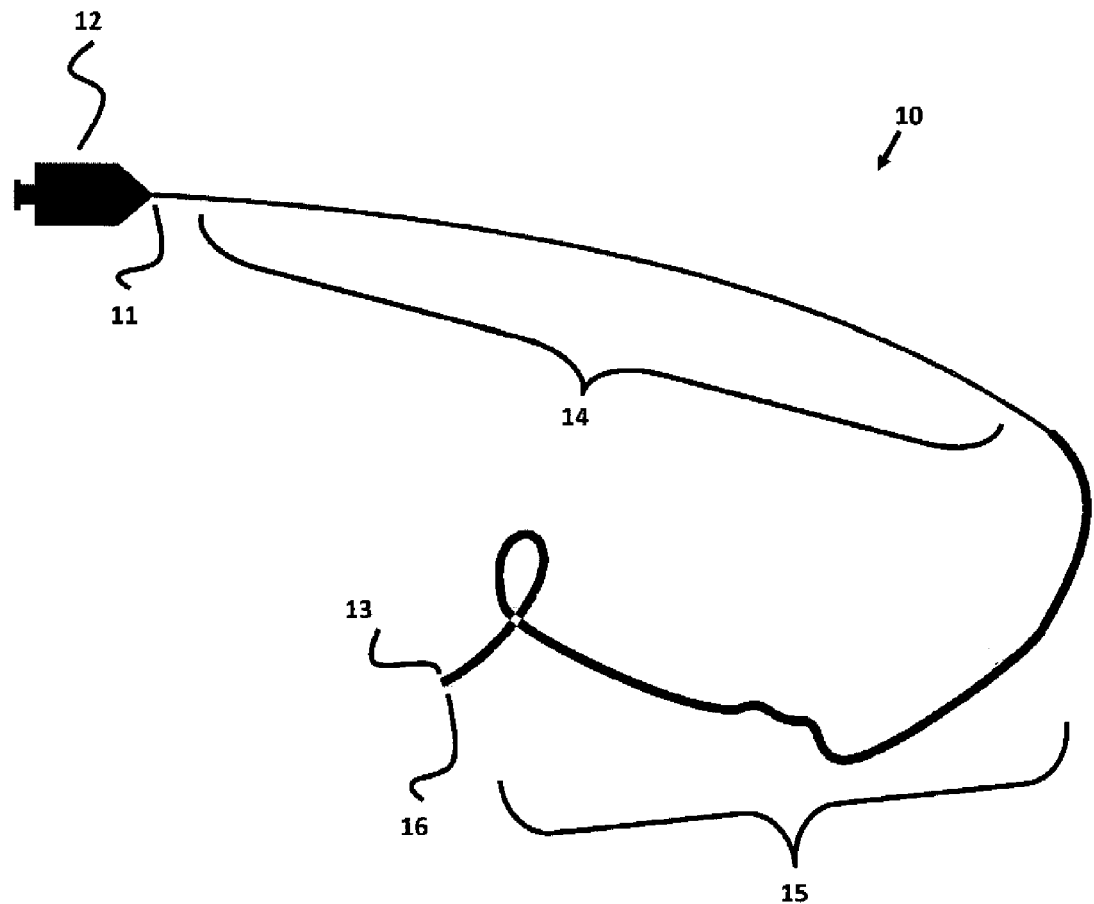
FIG. 1 illustrates the prior art components of a catheter and/or guidewire system.

FIG. 1 illustrates the prior art components of a catheter and/or guidewire system 10. For ease of explanation and use herein, and when appropriate, catheters and guidewires will be referenced herein as products. The overall length of the product system 10 is typically 175 centimeters to 195 centimeters in length, and can be as long as 300 centimeters for more difficult procedures that must travel further within the human body. The proximal end 11 of product system 10 is the end that a surgeon or medical professional holds during a surgical procedure. Proximal end 11 may include an attached handle structure, which is referred to as a torquer 12. Torquer 12 is gripped by the surgeon and physically rotated, which is referred to as torquing the product, with the intent to rotate the opposite end of the product, which is known as the distal tip 13.

Distal tip 13 may be bent slightly, either by the surgeon himself just prior to surgery or during production by the product manufacturer. Distal tip 13 is bent so that when product system 10 is physically rotated, or torqued, the bent tip also rotates and thereby points in a different direction—allowing the surgeon to torque the distal tip 13 into the desired vasculature pathway. The portion of the length of product system 10 nearest the proximal end 11 is referred to as proximal portion 14, and the portion nearest the distal tip 13 is referred to as distal portion 15. The precision cut products disclosed herein provide enough flexibility to allow easy navigation throughout a patient's complex vasculature while retaining enough torquability to smoothly transmit the surgeon's torquing movements from torquer 12 to distal tip 13. The guidewire 16 can be inserted into the hollow central portion of the catheter and may be thought of as being comprised of the same segments as the catheter, with a distal tip, a distal portion, a proximal portion, a proximal end, and possibly a torquer.

As discussed in the Background section, prior art machines for producing catheters and guidewires have severe drawbacks that limit the types of materials that may be machined into catheters and/or guidewires and the types of products that can be produced. As such, the discussion of the herein disclosed precision cut products will begin by describing a micro-cutting machine that is capable of machining a much wider array of materials, at a much wider array of dimensions while conforming to the strict tolerances required of delicate medical procedures. For example, polymer (plastic) stock material such as PEEK (polyetheretherketone) can be micro-machined on the micro-cutting machine described below into a highly flexible catheter at a relatively large diameter, whereas polymer material was previously impossible to machine because of its non-conductive qualities. In another example, stainless steel stock material can also be micro-machined on the micro-cutting machine described below into shapeable guidewires, whereas stainless steel was previously impossible to machine because its relatively high stiffness would require the beams to be cut so small (about 0.002 inches) that the resulting product would not be functional. One or more micro-cutting machines capable of machining non-conductive stock materials, as well as other stock material at previously impossible manners will now be described.

Figure 2:
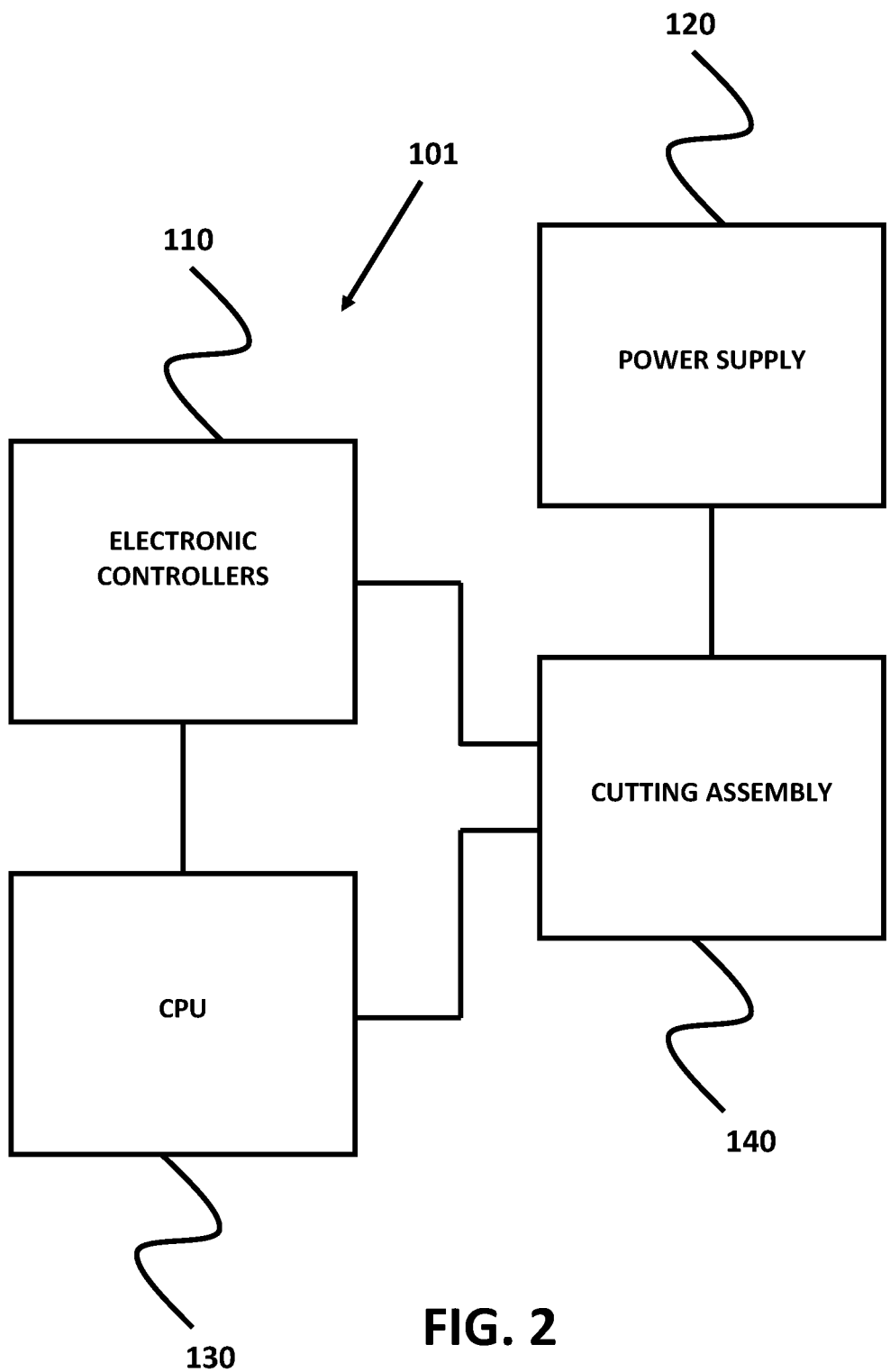
FIG. 2 illustrates a general overview of a micro-cutting machine in an embodiment.

FIG. 2 illustrates a general layout of the micro-cutting machine in accordance with an embodiment. Micro-cutting machine 101 includes cutting assembly 140, which generally has at least a pair of blades or cutting members and two or more stock material controllers, including feed and rotate motors, for precisely advancing and controlling the angle of the cylindrical stock material as it is cut and then preparing for a next cut. Cutting assembly 140 will be explained in much more detail below. Communicatively connected to cutting assembly 140 are electronic controllers 110 (which may be one or more electronic controllers, which are referred to as an electronic controller unit) for providing precise control signals to the cutting assembly 140 to control the position and speed of the blades and the position and angle of the stock material. The electronic controllers can also control the lights and a camera (an imaging system) for imaging the stock material before and after cuts and collecting data generated by the imaging system. A central processing unit 130 (such as a personal computer that includes a display, input and output systems, a storage system, etc., or some other type of CPU) receives user input, controls the electronic controllers 110 and the cutting assembly 140, and processes data generated by the imaging system to adjust the relative gap distance between the two blades. Alternatively, the CPU 130 could communicate directly with the imaging system and by-pass the electronic controllers 110. A power supply 120 supplies power to at least the cutting assembly 140, and possibly other components of the micro-cutting machine 101.

FIG. 3A illustrates a plan view of an embodiment of cutting assembly 140, which is mounted on a stationary frame assembly 200. The stock material 202 is fed into the cutting assembly 140 by the feed motor assembly 204, which can hold the stock material in a fixed position relative to the X-axis, the direction parallel to the spindle 206, and which can move the stock material along the X-axis by very small, controlled increments, so as to appropriately feed the stock material 202 into the cutting assembly 140, as further discussed below. The feed motor assembly 204 may comprise two feed motors (not separately shown), one for gripping the stock material 202 while it is being cut, as further described below, and one for moving the stock material 202 along the X-axis when the stock material 202 has been released by the first feed motor.

The stock material 202 shown in FIG. 3A is not illustrated as its actual size. The outer diameter of the stock material 202 can be 0.030 inches or less, or about 3 French on the French catheter scale, where a French is equal to three times the outer diameter of the stock material 202 measured in millimeters. Converting to inches, 3 French is equal to 0.039 inches, 4 French is equal to 0.053 inches, 5 French is equal to 0.066 inches, 6 French is equal to 0.079 inches, etc. Accordingly, based on the relative size of the cutting assembly shown in FIG. 3A, even a length of 6 French stock material 202 would be so small as to be almost impossible to see clearly, so the stock material 202 illustrated in FIG. 3A is much larger than its actual size for purposes of this illustration only.

The feed motor assembly 204 is mounted on a spindle 206 that is supported within the bearings of a bracket 208 mounted to the stationary frame assembly 200. A pulley 210 mounted to the spindle 206 is driven by a belt (not shown) that is, in turn, connected to another pulley (not shown) below the pulley 210, which is connected to a rotational motor (not shown) mounted within the stationary frame assembly 200. The rotational motor is a stepper motor, or the like, that is capable of extremely precise computer controlled movement. Based on programming provided through the electronic controllers 110 and the CPU 130 (such as through a user interface that allows a user to change certain parameters of operation of the electronic controllers 110 and therefore various components of the cutting assembly 140), the rotational motor can be programmed to cause the pulley 210 to rotate a specified number of degrees, so as to rotate the spindle 206 and feed motor 204 by the same specified number of degrees. Hence, the entire feed motor assembly 204 rotates, along with any gripped stock material 202 when the pulley 210 and spindle 206 are rotated by the rotational motor. Alternative embodiments could include different arrangements of the feed motor assembly 204 and the rotational motor, such as a feed motor assembly that only moves the stock material 202 along the X-axis and a rotational motor that grips and turns the stock material 202 when it is not being fed along the X-axis.

In order to better illustrate the relationship between the various components of the cutting assembly 140, the stock material 202 is shown exiting the feed motor assembly 204 supported by an elongated feed trough 212, which extends from the feed motor assembly 204 to one side of the cutting area (where the stock material 202 is cut by the blades 214, as further described below), and then extends from the other side of the cutting area to an output area 216. In reality, the length of the feed trough 212 between the feed motor assembly 204 and the cutting area would be relatively short. This enables the feed motor assembly 204 to be much closer to the cutting area, such that the stock material 202 would be cut almost immediately upon exiting the feed motor assembly 204. Keeping the length of the stock material 202 short between the feed motor assembly 204 and the cutting area helps to better control the stock material 202 while it is being cut, i.e., preventing the stock material 202 from moving along the Y-axis, the direction perpendicular to the spindle 206, or rotating while the stock material 202 is being cut.

It should also be noted that most of the stock material 202 is likely to be substantially rounded in shape, although other shapes could also be used. The stock material 202 has both width and height, giving it a Y-axis and Z-axis position, where the Z-axis is vertical to a plane including the X-axis and Y-axis. The feed trough 212 is intended to passively guide the stock material 202 as it is moved along the x-axis, which it could do in many different ways, such as through the utilization of precisely located guide posts or elongated members or a guide path that maintains the stock material 202 in a desired position relative to the Y-axis and Z-axis. The guide path of the feed trough 212 for rounded stock material 202 is preferably V-shaped, as illustrated by the cross section shown in FIG. 3B, wherein the stock material 202 lies in the bottom of the point formed by the V-shaped guide path within the feed trough 212.

As noted above, the cutting area is defined by a small gap between the two sections (prior to and after the cutting area) of the feed trough 212 where a pair of opposing blades 214 cut the stock material 202. In an embodiment of the application, the two blades 214 can be either semiconductor dicing blades or standard "tooth" type blades formed of a carbide material, such as tungsten carbide, to improve wear resistance. The submicron grain size of tungsten carbide and similar composites works well because they are less brittle, extremely hard, and can maintain their sharpness even at very small blade thicknesses. In an embodiment, additional different types of cutting instruments and systems could be utilized in place of the blades 214, such as water jet cutting systems, flame or oxyfuel cutting systems, plasma (arc) cutting system, electric discharge machining (EDM), etc., although not all of these systems are appropriate for use when cutting non-metal stock material or even certain types of metal stock materials, such as softer metals and less conductive metals. Given the variable operation of such additional types of cutting systems, it may also be necessary and/or desirable to change the orientation of the cutting assembly 140 and/or the stock materials 202 so instead of bringing the cutting point of the blade or system down along the Z-axis, the cutting point may be moved in the X-axis, or the cutting point may be held stationary while the stock materials is moved relative to the cutting point. All such alternative cutting systems are anticipated herein. Hence, when reference is made herein to a "dual blade" system, it is to be understood that any type of alternative cutting member or cutting system could also be used, depending on the application involved.

An embodiment for cutting plastic utilizes a tooth type blade with approximately 56 teeth. When cutting PEEK (polyetheretherketone) and other plastics with this blade type, a blade thickness of approximately 0.006 and 0.008 inches works well. When cutting nitinol, stainless steel and other hard metal and composite materials, a diamond semiconductor dicing blade with a thickness of approximately 0.002 inches works well. Given such thickness, the size of the open cutting area between the two sections of feed trough 212 represented in FIG. 3A is not to scale and is exaggerated in size in order to more clearly illustrate the opening of the cutting area. Of course, the blades 214 shown in FIG. 3A appear to be much larger in diameter than they really are as well, especially since, in most cases, they are only required to make very shallow cuts in the stock material 202. Since the stock material 202 could be formed of any type of material having any size diameter, such larger stock material would obviously need to be cut with thicker blades having larger diameters than those used to cut guidewires and catheters.

As will be further noted below, the embodiment does not require the stock material 202 to be of a metallic composition so its location can be electrically sensed by the blades 214 before a cut can be made. The embodiment can be used to cut any type of material, whether metallic or non-metallic, such as PEEK, a semi-crystalline, high temperature thermoplastic that is ideal for use in catheters due its high modulus of elasticity resulting in torqueability and the ability to hold a shape, and combinations of metallic and non-metallic materials. Although the general belief in the art has been that lower cutting speeds were necessary, especially when cutting PEEK, to reduce spur generation in the area of each cut, this was found not to be the case; much higher rotational speeds of the blades 214 worked well to reduce spur generation and provide exceptional accuracy. The embodiment also cuts other materials, including stainless steel and metallic composites at very high speeds with no burrs and with exceptional accuracy.

The blades 214 are located within a blade enclosure 218 (shown without its top in FIG. 3A so the interior can be viewed) through which air can be pumped to cool the blades 214 and the stock material 202, and through which debris cut from the stock material 202 can be removed. The hoses 220 of the air handling system can be used for pumping air and/or vacuuming air from the blade enclosure 218. The blades 214 can also be water cooled, as is known in the art.

In order to drive the blades 214 directly at higher speeds without requiring more expensive motors and additional complications, each of the blades 214 is attached to a spindle 222, that is oriented parallel to the X-axis. Each of the spindles 222 is driven by a belt 224 that is rotated by a pulley attached to the spindle motor 226. The spindle motor 226 is program controlled through the electronic controllers 110 and the CPU 130. The blades 214 are driven indirectly in this manner so as to achieve greater rotational speeds than would be possible or practical with a direct drive arrangement. For example, the spindle motor 226 is capable of running at approximately 4,000 revolutions per minute (rpm) over an extended period of time without stressing the spindle motor 226 or any of the bearings supporting the pulley. The aspect ratio between the pulley and the spindle 222 is approximately 6:1, so the slower rotating spindle motor 226 is capable of rotating the spindle at approximately 24,000 rpm, the desired speed for cutting PEEK and other materials. A direct drive motor capable of operating at 24,000 rpm would be significantly more expensive, require different bearing assemblies, and likely have a significantly higher failure rate.

The combination of the blade 214, the spindle 222, the spindle motor 226 and pulley, and the belt 224 is referred to herein as a "cutting assembly", but the same term would apply if a different cutting system without blades was being used as well. Each cutting assembly is attached to a blade stepper motor 228 that controls the Y-axis location of each blade 214. The stepper motors 228 are mounted on a movable frame assembly 230, as further described below. Each of the stepper motors 228 are program controlled through the electronic controllers 110 and the CPU 130, or can be manually adjusted through the control knobs 232.

To cut a piece of stock material 202 so as to leave a resultant beam, as further described below, of a specified dimension, each of the stepper motors 228 are adjusted to a predetermined location such that the blades 214 are close but not touching, and a cut is made in the uncut stock material 202 with both blades at the same time. The manner in which both blades cut the stock material 202 simultaneously is further described below. Once the cuts are made, the resultant beam is measured to determine if it is of the desired dimension. The stepper motors 228 are then adjusted along the Y-axis to move the cutting assemblies inward toward each other or outward away from each other, and another cut is made to the uncut stock material 202. This process is continued until the desired resultant beam dimension is achieved, at which point a series of cuts in the uncut stock material 202 is carried out.

By mounting the cutting assemblies on the stepper motors 228, it is possible to precisely control the Y-axis location of each blade 214 and to accommodate a larger variety of different stock materials 202, such as raw wire, tubing, and other shapes and sizes of cylindrical stock materials 202. For example, if a wide diameter catheter is to be cut from a relatively wide diameter piece of tubing, the stepper motors 228 can move the cutting assemblies apart to accommodate the larger than normal stock material. In another example, it may be that a user wishes to micro-cut a piece of metal wire for a guidewire having 0.002 inch resultant beams at one end and 0.004 inch resultant beams at the opposite end, with a gradual transition between the two beam widths. In this example, the stepper motors 228 can be precisely controlled by electronic controllers 110 and processor 130 to position the blades 214 to make cuts resulting in the desired resultant beam width, whether that be 0.002 inches, 0.0025 inches, 0.003 inches, 0.004 inches, etc. Thus, almost any desired dimension can be machined at any specified location.

Both of the cutting assemblies and the stepper motors 228 are in turn mounted on the movable frame assembly 230, which is moved up and down along the Z-axis by a Z-axis motor (not shown) located within the movable frame assembly 230 and mounted on a non-visible portion of the stationary frame assembly 200. By mounting the cutting assemblies and stepper motors 228 on the movable frame assembly 230, it is possible to precisely control the Z-axis position of both blades 214 at the same time. The blade enclosure 218 can be designed to be mounted to the movable frame assembly 230, such that the blade enclosure 218 moves along with the blades 214, or blade enclosure 218 could include two slots within which the spindles 222 could move up and down apart from the blade enclosure 218. So as to better seal the interior of the blade enclosure, it is preferable to have the blade enclosure 218 move with the blades 214.

Also shown in FIG. 3A (by dotted lines so that underlying components are visible) is the imaging system of the embodiment, which primarily comprises a digital camera 234 mounted within an upper cowl 236 and upper and lower lights, not shown. The upper cowl 236 is mounted to the stationary frame assembly 200 so that the camera 234 does not move along the Z-axis as the blades 214 move. The camera 234 is positioned directly over the cutting area and is focused on a portion of the stock material 202 as it is being cut and just after it has been cut, as further illustrated in FIGS. 4 and 5.

The camera 234 could be any of a number of commercially available high-speed digital video cameras as long as it is capable of capturing high quality pixilated video image data. In an embodiment, the camera is a model AM-413T digital microscope camera, manufactured by SunriseDino of New Hyde Park, New York. The more interesting aspects of the imaging system are the manner in which the stock material 202 is backlit and illuminated in order to increase contrast around the edges of the cut stock material 202 and how the digital image processing is capable of precisely measuring both cuts and the resultant beams.

Figure 4:
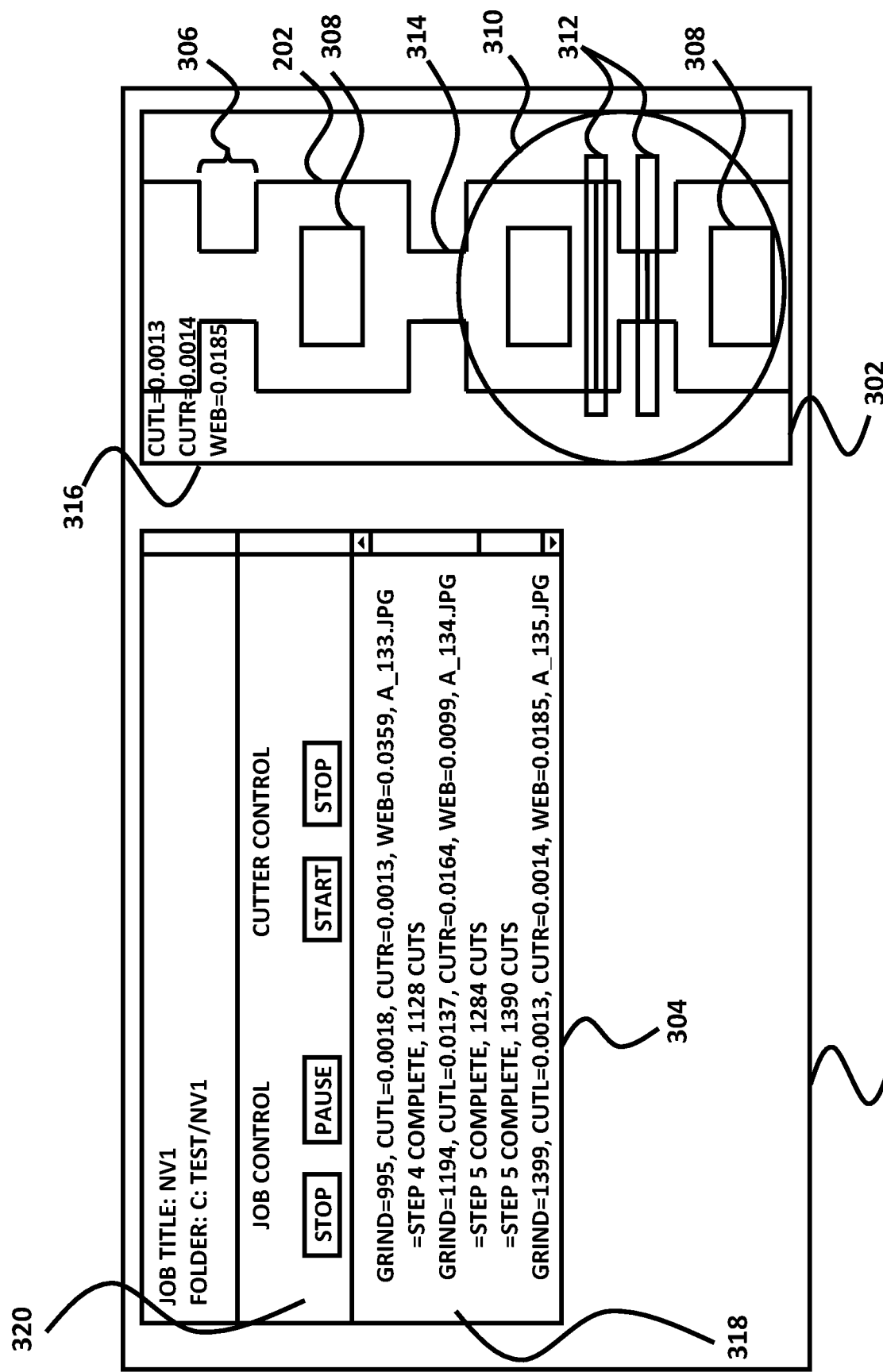
FIG. 4 illustrates a desktop image generated by the imaging system and CPU of FIG. 2 depicting the stock material once it has been cut by the cutting assembly.

FIG. 4 is an illustration of a desktop image 300 generated on the display of the CPU 130. The desktop image 300 includes an imaging window 302 and a control window 304. The imaging window 302 displays digital video images of the stock material 202 as it is being cut and as it is being measured by the imaging system. The area 306 shows the stock material 202 just after it has been cut by the blades 214 and the blades 214 have moved beyond the focused view of the camera 234. The stock material 202 being cut in the example illustrated in FIG. 4 is a tube used to make a catheter that is being rotated ninety degrees (90°) after each cut. Once a cut has been made, holes 308 are formed in the walls of the stock material 202 that become visible as the stock material 202 is turned in order to make the next cut. As the stock material 202 advances along the X-axis of the cutting assembly, the stock material 202 passes in front of a backlight, illustrated by the circle 310.

Figure 5:
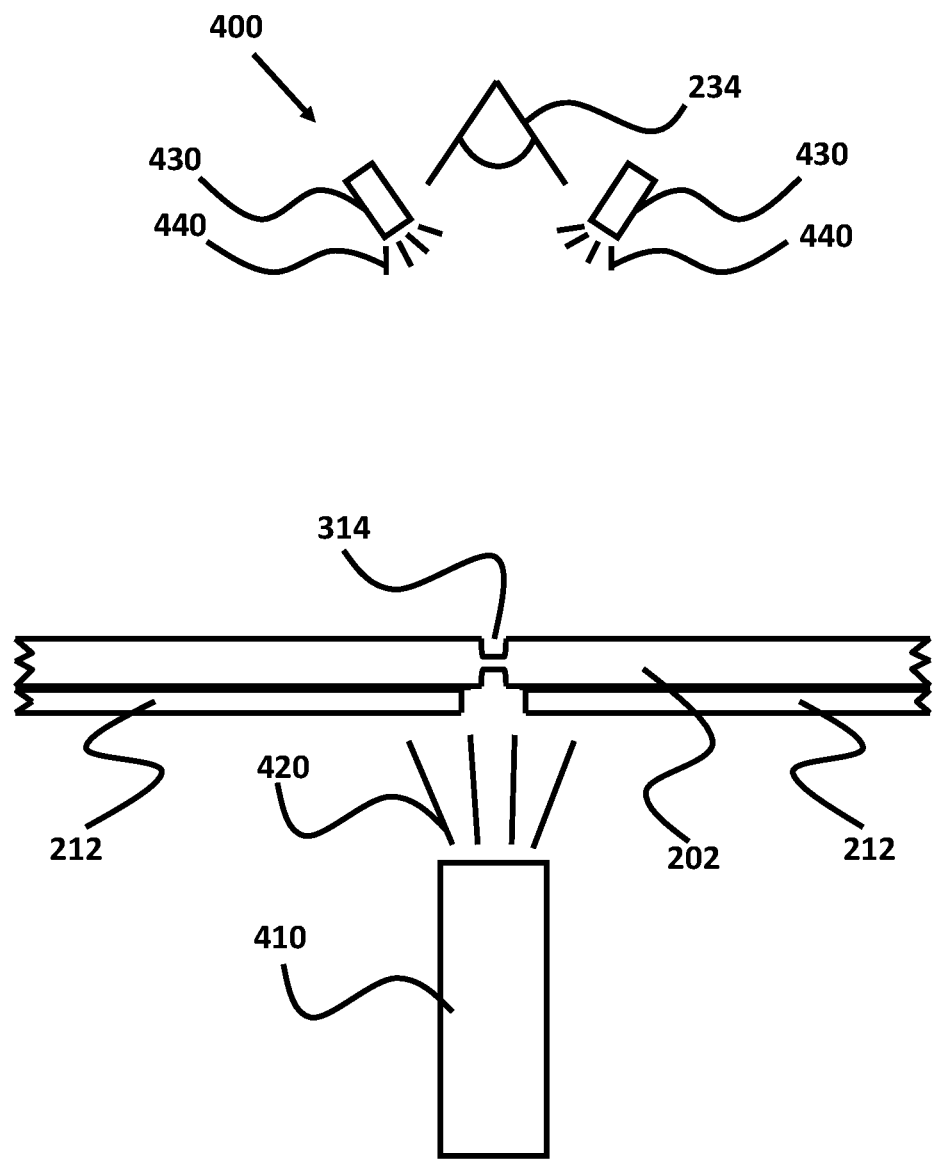
FIG. 5 illustrates the imaging system of the cutting assembly of FIG. 2.

Referring briefly now to FIG. 5, the camera 234 of the imaging system 400 is placed directly over the top of stock material 202, so that it may image and measure the stock material 202 and the resultant beam 314 formed by the two cuts. As discussed above, feed trough 212 leaves a gap through which the blades 214 can pass. The backlight 410 is an optical fiber, or a bundle of several optical fibers, through which red LED light 420 is provided by the imaging system. The optical fiber providing the backlight 410 is passed through a separately drilled hole (not shown) that enables the backlight 410 to shine around the stock material 202 and be visible to the camera 234. The backlight 410 is held in place below the cutting area by an anvil that is affixed to the stationary frame assembly 200 and is positioned to illuminate the stock material 202 just after it has been cut, although the stock material 202 can also be seen in imaging window 302 just as it is being cut. Camera 234 is communicatively coupled to processor 130 (not shown in FIG. 5) in order to provide feedback while the stock material 202 is being cut, and in order to store one or more images of one or more resultant beams 314.

A set of one or more green and blue LEDs 430 can be positioned above the stock material 202 and around the camera 234 to provide additional lighting 440 for a user to see the top side of the stock material for manual inspection purposes. The combination of a red backlight 410 and the green and blue LEDs 430 was selected because the camera 234 provides three color image channels of image data (red, green and blue) and the separately colored lighting enables the image data to be easily separated. The CPU 130 (and the software it operates) receiving the image data uses the red image channel for edge detection because it provides a high-contrast back lit image of the cut with no front side reflections that would confuse the measurement software being utilized by the CPU 130 to measure each cut. The green and blue image data created by the green and blue LEDs 430 and the camera 234 are transmitted through the green image channel and the blue image channel, respectively.

A purpose of the imaging system 400 is to monitor the exact location and size of cuts formed in the stock material 202. This information, meaning the image of a cut and resultant measurements, can be used in a number of different ways. For example, the images can be used to validate the accuracy and repeatability of the micro-cutting machine at or near in time to when the stock material 202 is being cut. If the images are being analyzed on the fly—while in the process of making the many cuts necessary to transform a piece of stock material 202 into a catheter or guidewire—the imaging system 400 can be used to stop production on that piece if a cut goes awry or the stock material 202 is out of tolerance.

Returning now to FIG. 4, although the camera 234 could theoretically capture an image of every single cut made to the stock material 202, doing so would generate an excessive amount of data that could not be competently reviewed at a reasonable cost by human operators. Instead, so as to provide adequate quality control, images are captured and recorded on a periodic or random (randomized test sampling protocol) basis, as further described below. While an image of the stock material 202 is being captured, as illustrated in FIG. 4, two visual overlays 312 are applied by the imaging system to the image data within the back lit area 310 to determine the length of each cut and the resultant beam 314, which is referred to as the "web" in FIG. 4. The overlays 312 measure across the stock material 202 at two or more different points, including at least the width or thickness of the stock material 202 and the width of the web or resultant beam 308.

The measurements taken by the overlays 312 are then analyzed by the CPU 130 and utilized to determine the length of the left cut, the right cut and the resultant beam or web 314. For example, by pre-determining the number of pixels per unit of measurement in the image being captured, and then counting the number of pixels displayed in the image data for the length of an object to be measured (using real-time image processing software operated by the CPU 130), it is possible to determine accurate measurements from the image data alone, without having to make use of mechanical measuring means. For example, if it is known that a piece of stock material 202 to be cut should have a width of 0.039 inches and the image data has a pixilation of 500 pixels per 0.05 inches, then approximately 390 pixels correspond to the width of the stock material 202. If a cut is then made in the stock material 202 from both sides leaving the resultant beam 314, and that resultant beam 314 is measured at 359 pixels, then the resultant beam 314 has a width of 0.0359 inches. Similar measurements can be made of each cut in the stock material 202 and these real-time measurements can then be displayed at 316 so the progress of the cutting operation can be monitored by an operator or the CPU 130.

When the width of the stock material 202 at the point of a cut is thicker or thinner than expected, the resultant beam 314 will still be within an acceptable range of its normal size because the position of the blades 214 relative to the stock material 202 is largely based on the centered position of the stock material 202, versus the known technique of basing each cut on the relative difference of the separate blades to the side of the stock material each blade is responsible for cutting. Hence, when thicker stock material 202 is cut, more stock material is cut away and when thinner stock material 202 is cut, less stock material is cut away, but in each case leaving a resultant beam of the desired size, versus generating thicker or thinner desired resultant beams, as is common in the art.

The control window 304 displays each measurement in a log section 318 of the control window that can be scrolled. As illustrated in FIG. 4, the CPU 130 has been programmed to instruct the imaging system to capture an image and measure the left cut, the right cut and the web on a periodic basis. For example, the first cut shown was grind 995 that resulted in a left cut (CUTL) of 0.0018 inches, a right cut (CUTR) of 0.0013 inches, and resulted in a web of 0.0359 inches, as noted above. The measurements and image file for grind 995 is then stored in a data file labeled A__133JPG. The grinds being recorded do not necessarily correspond to the same number of cuts that have been made, as more or less cuts may be made than are imaged, measured and recorded. Hence the steps illustrated as part of the log section 318 may correspond to a separate programmed process that keeps track of the number of cuts that have been made.

The control window 304 also includes selectable buttons 320 that allow an operator to stop or pause a job or start and stop the cutting process. The operator also has the option of assigning a title to each cutting job and to store the data associated with that cutting job in a particular folder on the CPU 130.

As previously noted, the CPU 130 provides programmed control of the electronic controllers 110, the rotational motor and the feed motor assembly 204 to control the movement of the feed stock 202 into the cutting assembly 140 along the X-axis. Once the stock material 202 has been fed into the cutting assembly and gripped by the feed motor assembly 204, the CPU 130 would instruct the rotational motor either to leave the stock material 202 at its current orientation or to rotate it by some degree specified by the CPU 130. Once the stock material 202 has been cut, the feed motor assembly 204 would advance the stock material 202 by some specified amount along the X-axis to position it for the next cut and grip the stock material 202. The rotational motor would then rotate the feed motor assembly 204 and the stock material 202 would be cut again. This process would then be repeated until all of the stock material 202 has been cut as desired.

By rotating the stock material 202 between each cut, the cutting assembly 140 can generate a cut stock material 202 with resultant beams 314 that are not all aligned in the same orientation along the length of the micro-machined product. For example, the stock material 202 could be turned ninety degrees from its angle at the time of the last cut, or many variations thereof, such as turned five or more degrees short of ninety degrees (i.e., 85 degrees) from the angle of the last cut, or even cut at random angles relative to the angle of the last cut.

An additional feature of the embodiment is the ability to measure the stock material 202 prior to being cut and using the resultant measurement to guide the depth of cuts. If stock material 202 was assumed to be 0.039 inches in diameter and it was desired to create a resultant beam 314 having a thickness of about 0.008 inches, then each cut would need to be 0.0155 inches deep. If the imaging system determined that the stock material 202 was only 0.032 inches in diameter instead of 0.039 inches, then the cutting machine would know that it needed to reduce the depth of each cut to 0.012 inches so as to leave the desired resultant beam 314 of 0.008 inches. However, as noted above, this is not necessary with respect to the embodiment where two blades 214 cut down from opposite sides of the stock material 202 because once the relative gap between the blades 214 has been established (that is relative to the cutting points of the two blades 214 or other cutting members), the gap dictates precisely the resultant beam 314 regardless of the outside diameter of the stock material 202. While the amount of material, or "depth of cut" is indeed different, there is no difference in the resultant beam 314 width.

In certain cases, however, it may be desirable to operate the blades 214 in an "offset cut" mode, wherein the blades 214 are not aligned in the same plane and deeper cuts are made. In this case, the cuts appear as independent cuts from each side (although cut simultaneously). The depth would then be important as each resultant beam, and the flexibility and stability of this type of structure, would be determined by the distance from the end of the cut to the opposing side of the tube. Although this type of structure could be made using the embodiment, it may not be terribly practical since it would require the cutting machine to image and measure the stock material 202 before each cut was made and to adjust the stepper motors 228 on the fly in the event it was determined that the stock material 202 was of the wrong diameter in order to change the depth by which the cuts are made.

Accordingly, the embodiment presently relies upon a quality control technique that measures only some of the cuts after they have been made instead of every cut. This enables the system to monitor the quality of the stock material 202 and other aspects of the system, but does not necessitate changing how the system is operating from cut to cut. For example, in the event stock material 202 was out of specification, it is not likely that its diameter would only vary at a single isolated point. Rather, if stock material 202 was out of specification at one point, it would likely be out of specification along of a length of the material or be out of specification at multiple individual points, one or more of which would be detected through the quality control technique. Large variations in the diameter of the stock material 202 may make the stock material undesirable for certain applications, so if this was determined, the cutting assembly 140 could be stopped and the product discarded once detected.

As stated, a main purpose of the micro-cutting machine is to make pairs of cuts (but not necessarily opposing) on cylindrical stock material to form flexible and torquable products, such as guidewires, catheters and other similar types of devices, all referred to herein as "products". While it is known in the art to create a flexible and torquable guidewire and catheter by making a single cut with a blade into a side of a cylindrical piece of stock material (metal wire and/or tubing), and then rotating the material and making an opposing cut on the opposite side of the stock material with the same blade. When this process is performed along all or part of the length of the stock material, the diameter of the stock material is reduced in numerous places, which increases the flexibility of the resulting product, but since the product retains the same overall outside diameter, the resulting product is able to retain much of its torquability. While the stock material cut in this fashion is usually cylindrical, since the cuts are made from opposing sides or nearly opposing sides toward the middle, it is helpful to think of the stock material as having a first side and a second side, even though in reality the stock material is substantially round and has only a single side.

Figures 6A, 6B:
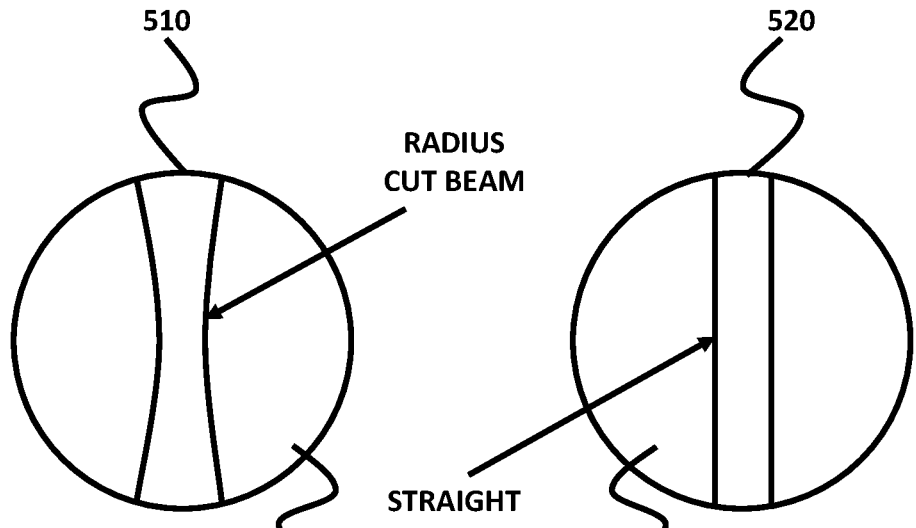
FIGS. 6A, 6B and 6C illustrate different views of a product cut in accordance with an embodiment.
Figure 6C:
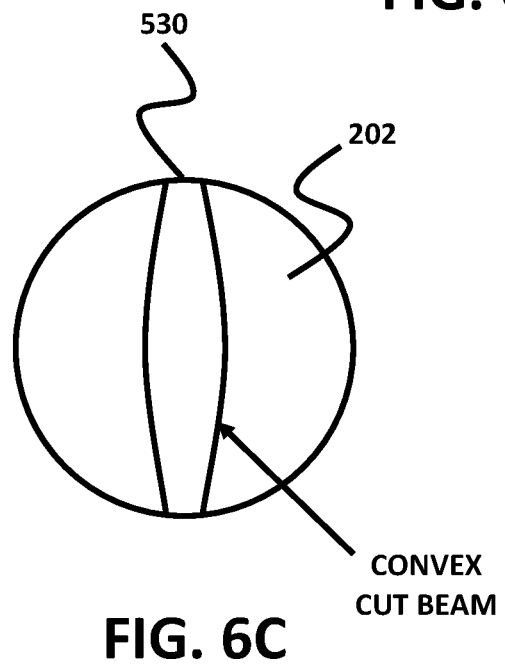

FIG. 6A illustrates the resulting beams that are generated by circular blades that cut from a first side and then a second side, a resulting beam that can also be generated through utilization of the embodiment. FIGS. 6B and 6C illustrate resulting beams that can only be generated through utilization of the embodiment. A cross-sectional view of solid stock material 202 is shown in FIGS. 6A, 6B and 6C. Based on existing technology, when the solid stock material 202 has been cut on the first and second sides (either all at once, as is presently disclosed, or on the first side and then on the second side, as is known in the art), a resultant beam 510 would remain. This type of resultant beam 510 is known in the art as a radius cut beam because it tapers from the circumference to the center point. Existing technology cuts the solid stock material 202 by advancing toward the solid stock material 202 along the Y-axis described above. As a result, the circular blade cuts the stock material 202 further in the central area than it can on the outer areas, always resulting in the radius cut beam 510.

Although a radius cut beam 510 is appropriate for some uses, it is not ideal from a torquability and safety perspective. The reduced thickness of the central area of the radius cut beam 510 enables stress to build up in that area as the product is twisted, which can result in breakage of the product. Given that products are often used in intravascular procedures, any breakage is highly undesirable. Likewise, if there is any irregularity in the diameter of the product, which irregularity cannot be sensed by the cutting machine, the cutting machine will make a cut in the product based on its programming alone. Hence, using the example provided above, if a guidewire was 0.039 inches in diameter and it was desired to create a resultant beam having a thickness of about 0.008 inches at the central area, then each cut would need to be 0.0155 inches deep. If the guidewire, however was only 0.032 inches in diameter and the cutting machine used electromagnetic sensing, instead of real-time imaging, then each side would still be cut by 0.0155 inches, leaving a resultant beam of 0.001 inches, which would also likely result in breakage when inserted into a simple curve.

The presently disclosed cutting machine, however, operates by moving the dual blades 214 along both the Y-axis and the Z-axis and is capable of creating a variety of differently shaped resultant beams, including the radius cut beam of FIG. 6A, as well as the straight cut beam of FIG. 6B and the convex cut beam of FIG. 6C. To create the straight cut beam, the cutting assemblies are moved above the stock material 202 along the Z-axis and adjusted along the Y-axis to create a distance between the blades, or other cutting member being used, sufficient to create a resultant beam of a desired thickness, then the cutting assemblies are brought down along the Z-axis and across the stock material 202. Hence, the machine is able to produce straight cut resultant beams, like resultant beam 520. A straight cut resultant beam 520 will enable greater and more consistent flexibility, due to the linear shape of the resultant beam, while retaining at least the same torquability as the radius cut beam, without the increased possibility of breakage.

To adjust the relative gap distance (or the resultant beam) between the blades or cutting members, a cut can be made, the resultant beam measured, and the cutting assemblies can be further adjusted along the Y-axis until a resultant beam of the desired width has been created. Alternatively, a reference stock of a known width can be placed between the blades/cutting members until both blades/members touch the reference stock.

As noted, a radius cut beam 510 or a convex cut beam 530 could be created by the herein disclosed micro-cutting machine by moving the cutting assemblies inward and outward along the Y-axis as each cut is being made. It would also be possible to make a variety of other types of cuts and resultant beams by varying combinations of elements at the same time, such as rotating the stock material 202 with the rotation motor as a cut is being made, or rotating the stock material 202 and moving the cutting assemblies along the Y-axis at the same time. For example, a spiral cut could be made by leaving the cutting assemblies at a set Y-axis position while the stock material 202 is rotated by the rotational motor. Angular cuts could also be made by mounting the dual blades 214 on a pivot point of some type, or by moving the stock material 202 at a desired angle relative to the Y-axis. In addition to cutting the stock material 202 in the manners already described, only at the specified angle, other types of cuts could be possible, such as V-shaped notch cuts and the like. As these types of cuts have not been possible before, the advantages of the different cuts is not yet fully known, but it can already be anticipated that a convex cut beam 530 would have even better flexibility and torquability properties than either the straight cut beam 520 or the radius cut beam 510.

As previously noted, the automated feedback and control process carried out by the imaging system 400 and the processor 130 can account for slight variances in cutting blade variations or in variations or imperfections of the stock material itself. The resultant beam, as discussed above, is the critical dimension and could be affected by even a single blade variation (such as a single blade tooth being too long) or by a variation of the diameter of the stock material throughout its length. All these factors are of course integrated into and manifest themselves in the resultant beam dimension. The precise measurement and adjustment capabilities of the embodiment result in unprecedented precision. Upon measurement of the resultant beam, the centering of the resultant beam with respect to the located stock surfaces, and the alignment of the two cuts to each other, the processor 130 can make adjustments to bring all parameters into alignment to create precise resultant beam widths. This process can be executed at the beginning of manufacture, as a set-up process, as one or more cuts are being made, as a periodic check, or as each and every cut is being made. The software run on processor 130 can be used to validate the repeatability of the micro-cutting machine, possibly reducing the number of measurements necessary while cutting a piece, or rendering continuous measurements unnecessary.

The micro-cutting machine of the embodiment, as previously noted, is capable of micro-cutting a wide variety of stock materials. Traditional single-blade micro-cutting machines make use of electromagnetic sensing of the precise location of the stock material relative to the single blade, thereby requiring the use of stock material that is conductive. This condition rules out the use of plastic tubing stock material or any other non-conductive or minimally conductive material (referred to herein as "non-conductive" even if the material has some relatively low conductivity that is insufficient to be cut by prior machines).

As discussed, the high definition images and measuring capabilities of the imaging system and the precise positioning of the cutting assemblies of the embodiment are much more accurate than relying upon sensing a surface of the stock material because the stock material itself can have an imperfect or inconsistent diameter. Therefore, the herein disclosed micro-cutting machine is much more accurate and can therefore cut finer dimension resultant beams with greater reliability. The physical arrangement of the components of the cutting assembly 140 and the stock material 202 make it possible to cut harder materials with less natural flexibility, like stainless steel, because the resultant beams can be cut very narrow while retaining precision. The dual blade micro-cutting machine of the embodiment is therefore fully capable of cutting stainless steel catheters and guidewires (greatly desired by surgeons for its ability to hold a shape—allowing the surgeon to personally shape the tip of a stainless steel guidewire to match the patient's endovascular system just prior to use), plastic catheters and guidewires (desirable for their great flexibility at relatively wider diameters), and other non-magnetic stock materials for all types of products.

Flexible yet torquable products are formed by repeating micro-cuts throughout either the entire length of a piece of stock material, or along one or more portions of the piece of stock material. Ideally, the pairs of cuts (a pair of cuts refers to one pass by the dual blades even though the cuts may not be opposite) are ideally made in a rotating pattern along the longitudinal axis of the cylindrical stock material. A rotating pattern is preferred because making all cuts at the same angle creates a product that is biased toward flexing in one direction—perpendicular to the resultant beam. If the stock material is rotated about its longitudinal axis between a prior cut and a next cut or a prior pair of cuts and a next pair of cuts, then the resultant beams are not all aligned in the same plane and the flexing bias is lessened or eliminated. This rotation between cuts is facilitated by feed motor 204 and the rotational motor, illustrated in FIG. 2. Feed motor 204 grips the stock material 202 as the rotational motor rotates the stock material 202 along the X-axis (the longitudinal axis of the stock material 202), according to directions received by electronic controllers 110 and determined by processor 130. The rotation between pairs of cuts is referred to as a variance, and is measured in the degree of rotation about the longitudinal axis of the stock material.

Figure 7A:
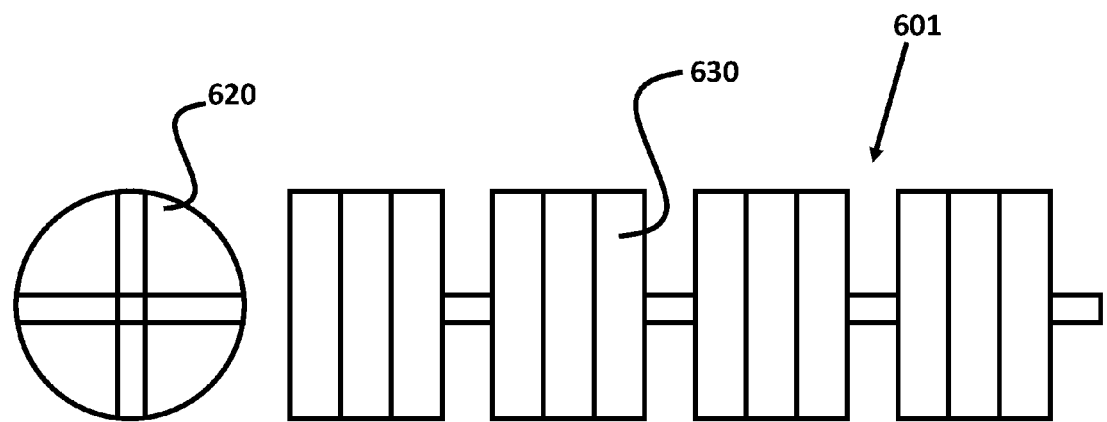
Figure 7B:
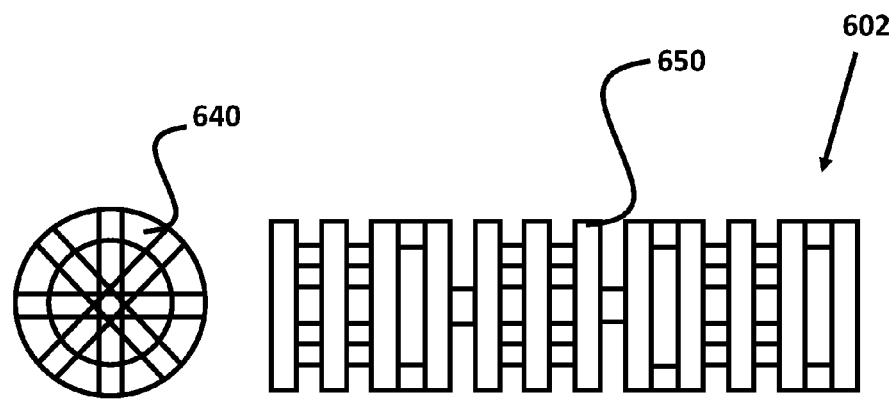

FIGS. 7A and 7B illustrate two examples of a rotating pattern of pairs of cuts and resultant beams. FIG. 7A illustrates a ninety degree variance guidewire 601 that was micro-cut using the dual blade micro-cutting machine of the embodiment. Cross-sectional view 620 illustrates the two different angles at which pairs of cuts are made when the stock material is rotated ninety degrees between cuts. Plane view 630 illustrates how such a guidewire 601 appears along its length. FIG. 7B illustrates a forty-five degree variance guidewire 602 that was micro-cut using the dual blade micro-cutting machine of the embodiment. Cross-sectional view 640 illustrates the four angles at which pairs of cuts are made when the stock material is rotated forty-five degrees between cuts. Plane view 650 illustrates how such a guidewire 602 appears along its length.

Figure 7C:
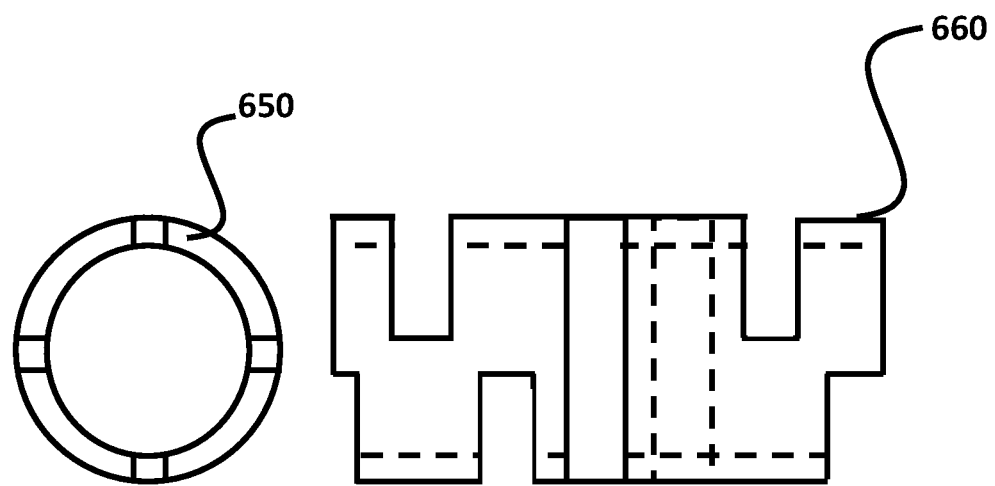
Figure 7D:
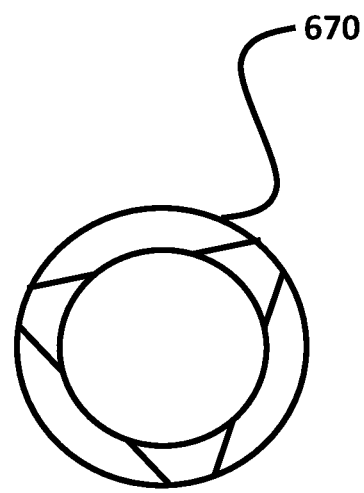
FIG. 7D illustrates just a cross-sectional view across a catheter, all in accordance with an embodiment.

FIGS. 7C and 7D illustrate two more examples of rotating patterns of cuts and resultant beams that can be produced with the dual blade micro-cutting machine of the embodiment. FIG. 7C illustrates a linear offset cut configuration 650 where a set of four beams are generated from offset cuts made in the stock material to produce the desired configuration 660. In FIG. 7D, a tribeam configuration 670 is generated by making a set of three angular cuts, resulting in triangularly shaped resultant beams.

A ninety degree variance, as illustrated by guidewire 601 in FIG. 7A, is significantly better than aligning all resultant beams in the same plane, but is still not ideal. The ninety degree variance results in resultant beams that are perfectly perpendicular to each other, which may cause the overall guidewire to be biased toward flexing in two directions—upward and downward, and to the left and to the right, if the guidewire is aligned like guidewire 601 in FIG. 7A. Using a forty-five degree variance between cuts, like guidewire 602 in FIG. 7B, can improve the flexing situation, because the resultant beams are now no longer oppositely aligned in only two planes. This form of cuts evens out the guidewire's flexing properties so that it is not biased in two distinct directions. In fact, an exemplary embodiment may utilize an uneven variance between cuts, such as ninety-five degrees, or forty degrees, so that the pairs of cuts, and therefore the resultant beams, truly spiral around the longitudinal axis—completely eliminating flexing bias in any one direction. Of course, the variance used in cutting a product can be even more complex. For example, advantageous results can be achieved by using a ninety degree variance between a first cut and a second cut, and then rotating the stock material slightly, such as by five degrees, before making a third cut and a fourth cut, the third cut and the fourth cut again using a ninety degree variance.

An additional feature of the dual blade micro-cutting machine of the embodiment is an ability to cut a serial number using the blades 214 or cutting member as controlled by the cutting assembly 140, electronic controllers 110 and CPU 130 into the stock material 202, so that the final product can be individually identified. The serial number or other form of identification could be formed by creating a series of cuts in the stock material 202 (possibly circumferentially so they can be read regardless of the rotation of the stock material 202) of varying width and/or varying spacing that could be read in a manner similar to a bar code.

Finally, it should be noted that while throughout the specification the micro-cutting machine has been described as utilizing a pair of cutting blades cutting simultaneously, it also may be possible to configure a micro-cutting machine utilizing two or more pairs of cutting blades or members operating concurrently. In this way, it may be possible to operate a plurality of resultant beams all at one time. In such a configuration, the pairs of cutting members would all be communicatively connected to electronic controllers 110 and processor 130, so that they can each be adjusted in unison to machine a product meeting the desired resultant beam parameters.

An alternative technique for forming the micro-cuts along a polymer product (or along a portion of the polymer product) involves thermo-forming all the cuts at once. The process works similarly to a polymer mold, and may begin with industrial polymer pellets in place of the previously extruded stock material. Industrial polymer pellets can be poured into a mold shaped with the desired product structure including the desired resultant beam widths, the desired pattern of beams along the x-axis, and the desired lumen in the case of a catheter. The mold and the polymer pellets set in the mold are then heated above the melting temperature of the particular polymer pellets, flowing the melted polymer into place within the product structure mold. The polymer is then cooled, or allowed to cool, and the now formed product is removed. Thus, a micro-cut guidewire or catheter can be formed without having to micro-machine individual cuts along the entire length of the stock material.

Several exemplary embodiments of precision products, which can be micro-machined on the above described micro-cutting machine, will now be described. In general, a guidewire is formed by micro-cutting a solid cylindrical stock material, and a catheter is formed by micro-cutting a tubular cylindrical stock material, but in the context of embodiments discussed herein, many other configurations outside of what are commonly known in the art are possible. In the prior art, conductive metal stock material was used for both types of products. As discussed above, different materials with superior performance properties, which could not be used in the past, can now be feasibly micro-cut into catheters and guidewires. For example, a guidewire could be formed of stock material other than solid metal stock, such as a tubular stock that has a wire inserted inside, or a laminar wire formed by coextruding a metal wire and another material around the wire.

Also in the prior art, the micro-machined material itself has been relied upon to provide most, if not all, of the physical body of the product and to almost exclusively dictate the product's performance characteristics. Further, in the case of catheters, a sealing tube disposed on either the outside or the inside of the tube was necessary to provide a fluid seal (i.e. so that the catheter would indeed function as a catheter and transmit fluid without leaking from its sides). These characteristics are not the case in accordance with embodiments where the micro-fabricated stock material (whether a tube or solid "wire"—called a monofilament, typically with respect to plastic wires) is merely an interspersed skeleton within a matrix of flexible material that is disposed within the machined gaps of the catheter or guidewire. The combination of the interspersed skeleton and the matrix (or base catheter material) provides an engineered hybrid body (catheter or guidewire) that dictates most of the structural integrity of the product (without reducing flexibility) and drives the product's performance characteristics. In the prior art, care is taken to ensure that the gaps cut into the stock material are free of any other material, while in embodiments the gaps are completely filled. In the prior art, the machined material may be coated with a very thin polymer layer, such as PARYLENE™, a trademark of Specialty Coating Systems, Inc., but this type of layer is chosen because it is conformal, rather than a filling layer, and because it is extremely thin, which are all characteristics aimed at minimizing the effects of that coating on the cut stock material. While the micro-cutting machine described herein is capable of making products from "stand alone" cut stock, which are described herein, additional capabilities are enabled by using non-conductive materials interspersed within the gaps cut into the "backbone" material to form a plastic matrix that provides a smooth continuous surface, which may be less thrombogenic due to less surface area. Thus the micro-fabricated skeleton is merely an interior feature of the product.

Many new products are made possible through use of the presently disclosed micro-cutting machine, many of which have not been possible to make with existing technology. Some, but not all of those products, are described herein and many more that are made possible with the present technology will become apparent to those of skill in the art. One such product is a hybrid guidewire that is formed from polymer stock material with a metal wire core running throughout. As the polymer outer layer is non-conductive, such a product could not be manufactured with existing technology, which required a metallic stock material to sense the appropriate place to make each cut. In such a product, using the herein disclosed technology, a number of options are available. One option involves only cutting through the polymer exterior with the micro-cutting machine, leaving an uncut metal core, or cutting through both the polymer exterior and the wire core. In the former case, a very thin wire core would need to be used in order for the guidewire to retain sufficient flexibility. The polymer stock material should be of a high modulus, meaning that the polymer material is rated to be relatively stiff. The polymer PEEK works well for this guidewire application, having a modulus of approximately 3700 megapascals (MPa). Other types of polymers could also be used having a modulus of approximately 1.4 gigapascals (GPa), such as PEBA, to approximately 138 GPa, such as, PEEK in combination with carbon fibers. Other combinations of materials could also be used, such as PEEK made with carbon or glass fibers, which would make the hybrid material stiffer and have a higher modulus.

Including a metal wire running through the centerline of the guidewire provides additional functionality, in that having such a metal wire provides a safety wire running down the middle, and facilitates shaping of the guidewire if the metal used is capable of holding a bend. Stainless steel, for example, is capable of holding a bend introduced by a user or surgeon in real-time when extruded at relatively thin diameters, and so may be an appropriate metal to use as the centerwire. The ability to hold the surgeon's precise bend is important because surgeon's often like to bend the tip of the distal end of a guidewire during surgery to precisely address unique circumstances associated with a particular patient. As noted above, in one embodiment, only the polymer exterior and not the wire metal core is micro-cut, which means that even if the micro-cut polymer outer portion breaks while deep inside a patient's vasculature, the centerline metal core should remain intact—allowing the surgeon to retrieve the entire guidewire despite the fact that the polymer portion has been damaged. The polymer outer portion and the solid metal wire core making up the stock material can be co-extruded at manufacture, before micro-cutting.

Alternatively, a tubular polymer stock material (formed with an empty lumen) can be micro-cut, and then the wire metal core can be inserted into the lumen. When the core wire is inserted into the tube in this manner, the diameter of the interior of the tube (the lumen) and the diameter of the exterior of the wire must be chosen carefully, with the entire assembly chosen to match a particular situation. For example, if the core wire is too large in diameter, the resulting product will be too stiff. Generally, a stainless steel core wire having a diameter of about 0.002 inches is appropriate to produce a floppy product. Adding another 0.002 inches or so to the wire creates a net flexibility equal to the superposition of the two. Hence, if the core wire is too much larger than about 0.004 inches, the tip of the product will likely be too stiff.

A second issue is shape-ability. If the wire is too small compared to the lumen, bending forces applied by the physician will not transmit to the wire (the wire will simply move within the annular space of the lumen). To account for this, a micro coil is typically inserted into the annular space to transmit the force to the 0.002 inch wire. The coil is typically made of platinum and includes radiopacity at the tip. The core wire can also be bonded to the lumen at the tip only, at the tip and proximal end, or at any of a number of other locations.

To accomplish micro-cutting only the outer polymer portion, the resultant beam should be machined at widths greater than the diameter of the centerline wire. In this manner, the centerline wire runs down the middle of the guidewire through and is essentially encased by the several resultant beams. In an embodiment, the polymer guidewire (with a metal wire core) has an outer diameter of approximately 0.014 inches, and the metal wire centerline has an outer diameter of approximately 0.002 inches. In an embodiment, the PEEK outer portion is micro-cut to create resultant beams of approximately 0.002 inches to 0.012 inches width, with the resultant beams cut with an angular variance of approximately 75 to 85 degrees.

Alternatively, if the polymer portion and the metal wire centerline are not co-extruded during production of the stock material, then the PEEK outer portion can be extruded to form an approximate 0.004 inch interior lumen—leaving enough space for a 0.002 inch outer diameter stainless steel wire to be inserted and bonded to the PEEK. The manner in which PEEK can be bonded to metal is known in the art. In an embodiment, a larger diameter centerline wire can be used and ground down to approximately 0.002 inches in diameter at one end before being inserted into the PEEK tube. In an embodiment, a tapered centerline or core wire could be ground down to a taper at one end so as to further modify the flex profile.

Additional features can be added to the polymer guidewire with a solid metal core centerline. The fact that the outer portion is polymer allows a hydrophilic coating to be covalently bonded to the outer surface. A hydrophilic coating increases the slipperiness of the guidewire, and thereby increases the guidewire's performance by easing travel through the patient's vasculature. The present embodiment improves the ability to hydrophilically coat the guidewire compared to prior art metal (usually nitinol) guidewires, because no tie layer is necessary between the metal surface and the coating. Of course, any coating not requiring a covalent bond could also be applied to the polymer surface. Such coatings may benefit from the polymer surface. As previously noted, another embodiment includes placing radiopaque markers on or in the centerline wire, thus allowing the guidewire to be tracked by X-ray devices while a surgical procedure is ongoing. Additional variations are also contemplated by the inventors, such as micro-cutting the polymer exterior around the metal core centerline in a spiral pattern so as to further distribute the flexibility of the device and to avoid biased flexing.

Another embodiment includes filling the cut gaps or fenestrations that form the resultant beams at or near the tip of metal core centerline with a polymer material to make a manufactured shaped tip that will hold the shape better. If the wire is made of stainless steel, which holds a shape well, the shape could be formed by the physician at or during the time of use. If the wire is made of materials that do not hold a shape as well, the wire can be placed in a mold of the desire shape before the gap filling material is applied. As the filling material cures, the molded shape will hold due to the cured filling material filling the gaps at the desired curves, i.e., less on the inside of the curve and more on the outside of the curve. This forms a very stable tip shape. The technique can also be used with shapeable metals so that the product has a pre-shaped tip and can also be further "fine tuned" by the physician during use.

Another product that can be formed using the above-described micro-cutting machine is a guidewire of approximately 175 to 195 centimeters in length and approximately 0.0014 inch outer diameter to approximately 0.0017 to 0.0018 inch outer diameter. As previously explained, the nature of prior art cutting systems have dictated that solid metal guidewires be cut from nickel titanium (NiTi or nitinol) versus other metals. The guidewire of the present embodiment can be formed from a solid, continuous piece of nitinol, stainless steel, platinum, or other metal that has been simultaneously cut on opposing sides at numerous positions along some length of the guidewire with the micro-cutting machine described above.

For example, a guidewire micro-cut from solid stainless steel stock material results in a highly torquable and relatively durable (because solid stainless steel guidewires will fracture much less easily than comparable guidewires made from other materials. Forming a guidewire from solid stainless steel stock material requires that the resultant beams be cut accurately to widths smaller than approximately 0.004 inches. These solid stainless steel guidewires may also be micro-cut utilizing the variances described above, and may also be coated with hydrophilic material, as is known in the art—although an intermediate step of coating the metal surfaces with a tie layer is required, as described above in the case of covalently bound coatings. Other stock materials besides stainless steel may of course be used as well to produce a solid metal guidewire.

Hybridized guidewires utilizing more than one type of stock material at different points along the length of the guidewire may also be formed. For example, one type of stock material can be micro-cut and used on the distal portion 15, while a second, different, stock material can be separately micro-cut and used for the proximal portion 14, with a bond holding the two portions together. For example, a guidewire may be formed with solid nitinol wire for the distal portion 15 and with stainless steel hypotube for the proximal portion 14. The nitinol wire can be pushed through the stainless steel hypotube so the distal portion extends beyond the end of the stainless steel hypotube forming the proximal portion 14. An embodiment for this example would limit the nickel titanium distal portion 15 to approximately 35 centimeters of the overall guidewire length (usually 175 to 195 centimeters overall as noted above), with the remaining length devoted to the proximal stainless steel hypotube. In this embodiment, both portions can be micro-cut to form resultant beams, or alternatively it may not be necessary to micro-cut the proximal hypotube portion. These hybrid guidewires may also be micro-cut utilizing the variances described above, and may also be coated with hydrophilic material using the known intermediate step of coating the metal surfaces when a tie layer is required, as described above. Other stock materials besides stainless steel and nickel titanium may of course be used as well to produce a hybrid guidewire.

The use of a stainless steel hypotube for the entire length of the catheter or some proximal portion provides a number of advantages, such as providing superior proximal support and pushability, which translates into more predictable distal vascular access. The greater stiffness associated with the stainless steel hypotube also offers the additional advantage of straight positioning within the guiding catheter in which it is inserted, which provides increased operator control of the distal tip. In other words, the stainless steel hypotube is stiff enough not to bend and snake up against the interior walls of the guiding catheter and flop around within the catheter as it is moved by the operator. Higher injection rates are also possible with the stainless steel hypotube due to its ability to withstand higher pressure within the guiding catheter as fluid is injected between the exterior walls of the hypotube and the interior walls of the guiding catheter. Finally, the smooth surface of the interior walls of the stainless steel hypotube also presents less friction and opportunity for a detachable coil, such as an embolic coil, to catch during insertion delivery.

Polymer catheters may also be formed by micro-cutting polymer stock material on the above described micro-cutting machine. FIGS. 8A and 8B illustrate a cross-sectional view of catheter stock material before being micro-cut (FIG. 8A) and after being micro-cut (FIG. 8B) using prior art cutting machines. The catheter 801 is formed from a hollow stock material that forms the interior area or lumen 810 which is defined or formed by the lumen wall 811 of the exterior stock material 812. When used in an intravascular procedure, a guidewire 870 can be placed through lumen 810, where guidewire 870 is usually of significantly smaller diameter than the diameter of lumen wall 811. The lumen gap 820, defined by the difference between the outer diameter of guidewire 870 and the inner diameter of lumen wall 811, allows a liquid, such as radiopaque dye for example, to be forced through catheter 801 while guidewire 870 is also in place.

There are a number of problems with cut catheter products using prior art micro-cutting machines as is illustrated in FIG. 8B. One significant issue is that the prior art machines are only capable of cutting the resultant beams with a concave cut because each blade is moved at an angle perpendicular to the length of the stock material and the blade is curved, so it cuts in an arc with more material in the middle of the catheter being cut than on the outer edges of the catheter. FIG. 8B exaggerates the significance of this difference (between the inner beam and the outer beam) to illustrate this point. If the blade has a significantly larger diameter than the diameter of the stock material, the difference will not be as big, but may still be of great significance because it weakens the lumen walls at exactly the wrong point, as further explained below. To avoid this problem, it is necessary for prior art machines to use blades having significantly greater diameters than the stock material so as to negate this difference as much as possible. Otherwise, the "hourglass" shape of the result beam places the larger width at the top and bottom—exactly where it is not wanted from a flexibility perspective—and places the thinnest width in the middle—also exactly where it is least desire.

When the micro-cuts in the exterior stock material 812 used to form resultant beam 520 penetrate too far into the exterior stock material 812, they can potentially pierce through the lumen wall 811. When this occurs, the lumen 810 of catheter 801 can no longer retain all of the liquid being forced through it. Furthermore, even if the micro-cuts used to form the beam 520 did not penetrate the lumen wall 811, the resultant lumen wall 811 may be too thin to withstand the pressure formed by the liquid forced through catheter 801, thereby causing the lumen 810 to break and liquid to leak out through resulting gaps or fenestrations. Regardless of the manner in which a leak occurs, leaks are almost always unacceptable. Unlike the prior art, with the micro-cutting machine described herein, each cut is made from top to bottom, or vice versa (perpendicular to the width, not the length), so the cuts are straight or convex, but not concave unless a concave cut is actually desired. Thus, the resultant beam is more uniform, more flexible because the beam width can be narrower at the outer edges, and less inclined to leakage because thicker walls, if desired, can be generated around the lumen.

In an embodiment of a polymer catheter, polymer lumen forming stock material, such as PEEK, may be micro-cut to provide even greater flexibility, with the micro-cuts purposely breaking through the lumen wall into lumen. To re-establish the fluid integrity of lumen, a polymer matrix can be formed around the cut outer portion of the catheter, filling the gaps or fenestrations in the lumen walls without filling the lumen itself. As further discussed below, this can be accomplished in a number of ways. Either before or after the matrix is formed, a thin liner tube having an outer diameter that is slightly smaller than the inner diameter of the lumen wall can be inserted through the catheter. The liner is used to smooth the lumen wall, decrease friction, add lubricity, help keep the polymer material forming the matrix from entering the lumen, and increase the burst pressure strength of the product, but the liner would not act as a fluid seal, which function is performed by the polymer matrix. This type of catheter, with a liner tube running throughout some length of the catheter formed of a cut skeletal body with a polymer matrix, is referred to herein as a two-piece polymer catheter.

In an embodiment of a two-piece polymer catheter, the outside diameter of the overall catheter is approximately 0.039 inches or less to approximately 0.091 inches or more. This is a relatively simple two-piece polymer catheter to produce because the micro-cuts may be formed without worrying about avoiding puncturing through lumen and forming fenestrations. In fact, cutting through the lumen walls can now be desirable because it further enhances flexibility. The liner tube is preferably formed of a highly flexible polymer material, as is known in the art, because the liner tube needs to be naturally flexible without micro-machining (micro-machining both the outer lumen-forming material and the liner tube would be cost prohibitive), and does not need to transmit torque (torque is transmitted through the length of the catheter by the micro-machined, skeletal, outer lumen forming material). Alternatively, the liner tube can be formed of other materials, such as polytetrafluoroethylene or PTFE, for example. The utilization of a liner tube, however, does generally reduce flexibility of the catheter when compared to other catheters that do not utilize a liner.

It is of course possible to effectively utilize a polymer catheter cut with fenestrations as described above even without the polymer matrix and without inserting a liner tube. Without the liner tube, a polymer catheter micro-cut to have fenestrations, but cut with the micro-cutting machine described above, will have extreme flexibility while retaining significant torqueability along its entire length. The catheter's lumen will not have fluid pressure integrity—a fluid forced through the lumen will leak out through the fenestrations caused by micro-cutting through the lumen wall—but other non-fluid materials may still be forced through the catheter and thereby forced deep into the patients' vasculature. For example, platinum embolic coils, commonly used to fill aneurysms in patients, may be effectively pushed through the polymer catheter with fenestrations without issue. This polymer catheter with fenestrations may provide the highest flexibility for a given catheter diameter because there is no stiffening due to liner tube stiffness, and therefore may be appropriate for highly curvaceous vasculature or used as a flow directed catheter when designed appropriately.

Figure 9:
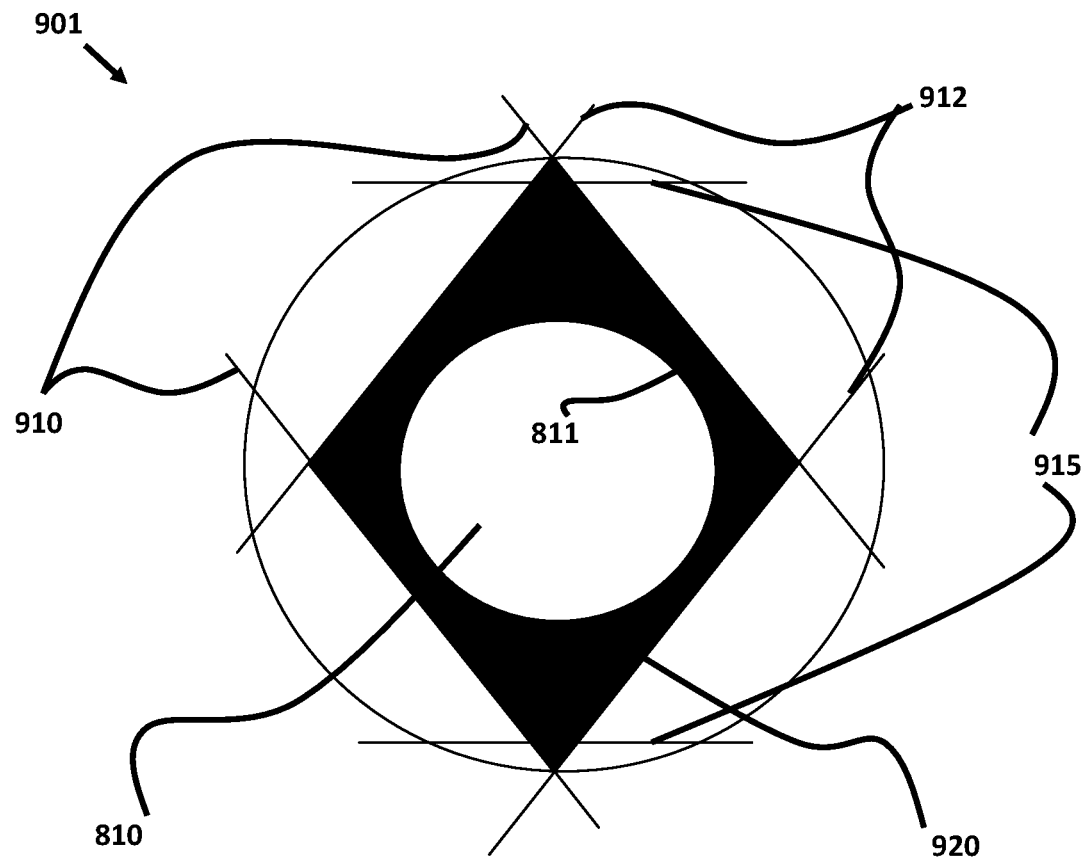
FIG. 9 illustrates a cross-sectional view of a micro-cut catheter without fenestrations in accordance with an embodiment.

Alternatively, a polymer catheter can be micro-machined in a different manner than that described above so that the micro-cuts forming the resultant beams do not puncture lumen and cause fenestrations. To produce this type of polymer catheter, at least four micro-cuts (two cuts or "passes" with the double blade system) are made in the exterior stock material, compared to the pair of simultaneous micro-cuts described above. FIG. 9 illustrates a polymer micro-cut catheter without fenestrations 901 and no liner tube. Micro-cuts 910 and 912 are made at four angles, each of which stop short of lumen wall 811, resulting in formation of a diamond-shaped resultant beam 920. The four cuts can be made in pairs (910 representing a first pair of cuts and 912 representing a second pair of cuts) so that the efficiencies of the dual cutting members described above can be used to full advantage. The dual cutting members can cut the exterior stock material 812 from opposing sides and cut inward, stopping somewhat short of reaching lumen 810. Then, before moving the stock material along the X-axis as is described above, the stock material is instead rotated ninety degrees (or some other angle) so the dual cutting member can cut another complementary pair of micro-cuts 912 that stop equally short of lumen wall 811.

As is apparent in FIG. 9, resultant beam 920 is an approximate diamond shape—differing from the approximately rectangular shaped resultant beam 520 illustrated in FIG. 6B. How close the pairs of cuts 910 and 912 can come to puncturing lumen wall 811 depends upon the application for which the micro-cut catheter without fenestrations 901 will be used. If lumen 810 will be used to carry large quantities of radiopaque dye at relatively high pressures, for example, then it will be appropriate to stop well short of lumen wall 811 with cut pairs 910 and 912, thereby leaving a relatively thick diamond-shaped resultant beam 920 that can withstand high pressure liquid flow. If, on the other hand, lumen 810 will be utilized solely to carry non-fluid materials like platinum embolic coils, then resultant beam 920 can be machined much thinner by making deeper pairs of cuts 910 and 912.

The sharper edges of the diamond-shaped resultant beam 920 apparent in FIG. 9 can be reduced by making additional pairs of cuts, such as cut pair 915, before moving the stock material along the X-axis to the next desired resultant beam location. Alternatively, the sharp edges can be further smoothed by rotating the angle of the stock material during the cutting of a pair of micro-cuts. This step is much like the operation of a lathe, wherein the stock material is spun (via changing the angle of the stock material) while a tool is held in a relatively fixed position—the tool being the dual cutting members. In another embodiment, the micro-cutting machine described herein can be fitted with one or more boule saw blades (circular or round saw blades with teeth on the inside diameter), which when utilized to make the pairs of cuts will produce a much more rounded resultant beam 920. Of course the combination of the these techniques can be used to form a variety of wall thicknesses and shapes as desired such as more material at the top and bottom of the diamond (i.e., no diamond point at all, but a wider beam), and the left and right side might have a rounded cut (from rotating the stock) providing a relatively uniform wall thickness over a portion of the two sides.

A hybrid catheter, comprising different stock materials for proximal portion 14 and distal portion 15, can also be produced. In this embodiment, the catheter uses a high strength material as stock material for proximal portion 14, such as a braided plastic polymer or a stainless steel hypotube. Distal portion 15 is then formed from a more flexible (lower modulus) material, such as a polymer (PEEK or some other material)), or some other material selected for its desired properties. A polymer or PTFE (or equivalent) liner tube can then be inserted, running up to the entire length of the hybrid catheter and ensuring a smooth lumen surface throughout, while also facilitating binding proximal portion 14 to distal portion 15. Other forms of binding may also be required or desired. In this hybrid catheter, the relative lengths of the stiffer proximal portion 14 and the more flexible distal portion 15 can be optimized for the particular application, or even for the individual patient, if desired. Distal portion 15 can encompass more of the entire catheter length, if the procedure requires deep penetration of the complex vasculature of the brain, for example. In this case, the stiffer proximal portion 14 would consequently encompass less of the overall catheter length. Similarly, if a particular patient's vasculature differs greatly from the norm for a particular procedure, then the relative lengths of stiff proximal portion 14 and flexible distal portion 15 can be individually tailored to suit that individual's vasculature. Depending upon the stiffness of the proximal material, it may be advantageous (and perhaps safer) to reduce the length of the proximal portion 14 such that it cannot reach certain anatomy (such as the carotid siphon) or so that it remains within the length of another medical devices such as a guiding catheter.

Alternative embodiments include products having proximal portions 14 formed of stainless steel or other more rigid materials and distal portions 15 formed of highly flexible materials, such as PEEK or nitinol, with the proximal portion 14 joined to the distal portion by an intermediate joint, where the proximal portion 14 is firmly secured to the distal portion 15. Hybrid products of this type enable a highly flexible, steerable and torqueable distal portion 15 (such as a PEEK skeleton coated with a PEBA matrix, as described above and below) to be combined with a thick and strong proximal portion 14 that can be easily held and handled by a surgeon.

An embodiment comprising micro-cut catheters and guidewires including one or more layers of elastomeric material (any polymer or plastic material with especially elastic properties) refilling micro-cuts will now be further described. This refilling, reflowing or laminating technique can be applied to any of the above described catheters or guidewires with advantageous results. Additionally, this technique can be applied to prior art micro-cut catheters and/or guidewires to improve their performance.

Figure 10A:
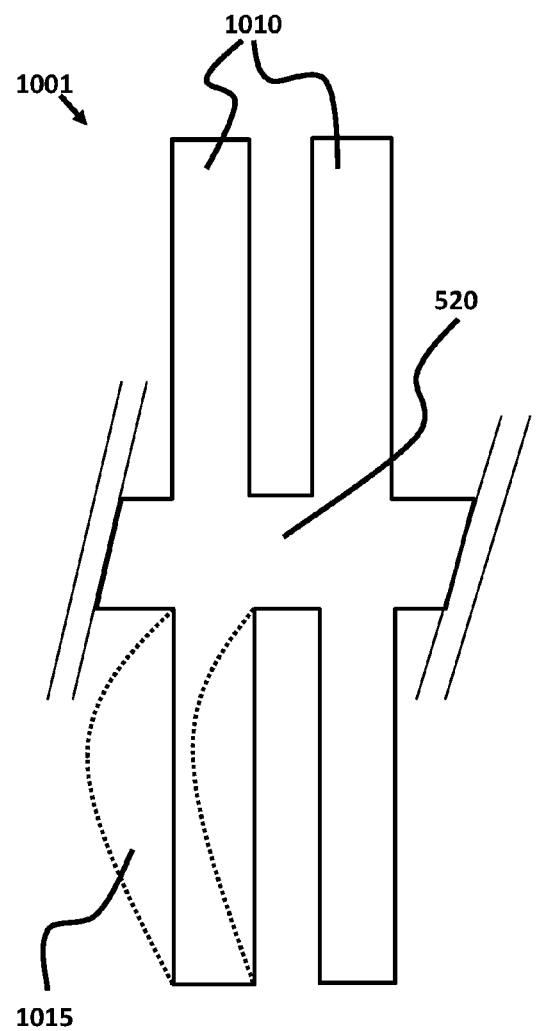
FIG. 10A illustrates a prior art exemplary deformation of a ring of a micro-cut guidewire.

FIG. 10A is an illustration of a micro-cut catheter or guidewire that shows a temporary deformation that may occur when a catheter or guidewire is bent, or subjected to torque, during the normal course of use of the device. This deformation may occur in guidewires and catheters micro-cut using prior art techniques as well as guidewires and catheters cut using the micro-cutting machine herein disclosed. The elastomeric laminate technique described above and further below alleviates this deformation in both guidewires and catheters, regardless of the manner in which they have been micro-cut. For purposes of convenience and simplicity, the elastomeric laminate technique of the present embodiment will be described below with regard to a micro-cut guidewire, but it should be understood that the same discussion applies equally to micro-cut catheters, as described above.

In FIG. 10A, a simplified view of a segment of a non-laminated guidewire 1001, micro-cut to form resultant beam 520 and rings 1010. When a non-laminated guidewire 1001 is highly flexed, as will occur when the guidewire is deeply inserted into a patient's vasculature, rings 1010 may be stressed and may bow as a result. This bowing is represented in FIG. 10A by the dotted line 1015. Bowed ring 1015 is stressed and in a deformed position, which causes the entire non-laminated guidewire 1001 to transmit a surgeon's torque inefficiently and erratically from torquer 12 to distal tip 13. This is problematic because the surgeon would like to have complete control over distal tip 13. Torque may be transmitted more effectively from torquer 12 to distal tip 13 if rings 1010 can be kept in alignment while the guidewire is flexed throughout the patient's vasculature.

Figure 10B:
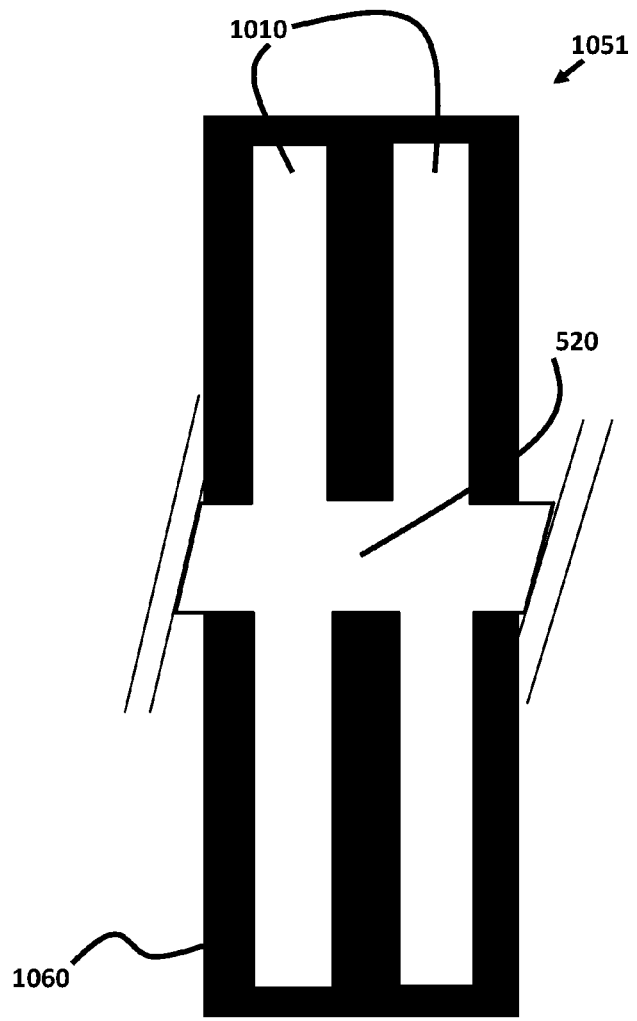
FIG. 10B illustrates an elastomer laminate applied to a micro-cut guidewire in accordance with an embodiment.

The reinforced matrix 1060 illustrated as the blackened area in FIG. 10B provides a solution to the bowed ring 1015 problem without compromising the flexibility of the product, but the reinforced matrix also serves many other useful purposes, in addition to solving the bowed rings problem. For example, the reinforced matrix 1060 provides cushioning to the rings 1010, help to limit total movement within desired ranges, and balances forces within the product by transmitting forces applied to one ring to the next ring, operating much like vertebrae disks in the backbone of humans and other vertebrates. As shown in FIG. 10B, the micro-cuts formed between the rings 1010 are refilled or reflowed with an elastomeric material that fills the gaps and coats the exterior of the guidewire 1051, as illustrated by the darkened area 1060. In essence, the micro-cut guidewire forms an internal, relatively rigid, but flexible and torqueable, skeleton for the product, while the elastomeric laminate provides a highly flexible integrated skin or matrix around the skeleton. When elastomeric laminate 1060 is used to fill the spaces created by the skeleton, the rings 1010 of the laminated guidewire 1051 are kept in alignment (or at least closer to alignment) due to the resistance created by the laminate to any pressure exerted against the rings 1010, even when the guidewire is flexed, or bent, throughout the patient's complex and curvaceous vasculature. By refilling the micro-cuts with an elastomeric material, the rings 1010 are forced to "bounce back" from any bowing which may occur when the guidewire is flexed. An added benefit of the elastomeric lamination is that if a resultant beam or a ring happens to break while inside a patient's vasculature, the guidewire can remain in one piece via the surrounding laminate material—significantly easing removal.

Elastomeric laminate 1060 is ideally an elastic material having a durometer (a measure of hardness) or modulus (a measure of stiffness) significantly below that of the stock material forming the rings 1010 and resultant beams 520 of the guidewire. This is so the laminate filling material does not have adverse effects on the overall guidewire flexibility. For example, if the guidewire is micro-cut from PEEK stock material, as described above, then a relatively soft and flexible elastomeric material such as polyether block amide (PEBA) can be used as the laminate filling. Such a combination is advantageous because PEEK has a modulus (stiffness) of approximately 3700 MPa, while PEBA has a modulus of approximately 10 to 500 MPa (depending on production considerations). As a result, the flexibility of the micro-cut PEEK skeleton or substructure will hardly be affected by the much more highly flexible PEBA laminate skin or matrix.

Nevertheless, in the event the addition of the PEBA skin or matrix does impede the flexibility of the micro-cut guidewire in some manner, the skeleton or substructure can be made even more flexible, thereby counteracting any impediment created by the skin or matrix, by altering the micro-cut pattern to include more micro-cuts along the length of the guidewire or catheter, thereby increasing its overall flexibility. Alternatively, each pair of micro-cuts can be made deeper resulting in thinner resultant beams and thereby alternatively increasing flexibility. While an increased number of micro-cuts or deeper micro-cuts may be undesirable in a non-laminated guidewire, the presence of the skin or matrix provides the additional safeguard of holding the skeleton or substructure together in the event of a breakage, so more micro-cuts and/or deeper micro-cuts are made possible with the presence of the skin or matrix. In this manner, the properties of the individual components can be engineered so that they perform as desired as a system, providing new and better overall performance.

The PEBA skin or matrix can be applied in a number of manners, such as coating an uncoated guidewire with the PEBA material in a machine that applies the coating and dries or cools the material in place before exiting the machine. A PEBA skin or matrix can be placed around a catheter in a similar manner by placing the catheter over an internal mold that fills the hollow central area, while the PEBA coating is applied and dried/cooled to hold it in place, then removing the internal mold so as to leave the resulting lumen 810. An alternative embodiment for applying the elastomeric laminate over the guidewire involves pulling a tube formed of the desired laminate material over a length of the micro-cut guidewire, heating the laminate-guidewire/catheter combination to a temperature above the melting point of the laminate material but below the melting point of the stock material, and then cooling the coated guidewire to form the skin or matrix.

With regard to a catheter, a liner or Teflon coated mandrel could be inserted into the hollow central area of the catheter while a tube is pulled over the exterior, such that when heat is applied to the tube and liner they melt together forming the skin or matrix and leaving the lumen. For example, PEEK has a melting point of approximately 343 degrees centigrade and PEBA has a melting point of approximately 134 to 174 degrees centigrade depending on how exactly the PEBA was produced. Therefore, a tube or liner formed of PEBA can be pulled over and/or inserted into either a portion of, or the entire length of the guidewire or catheter micro-cut from PEEK stock material, and then the combination can be heated to 175 degrees centigrade to form the skin or matrix. The PEBA laminate will melt into the micro-cuts between the rings 1010, but the PEEK rings 1010 and resultant beams 520 will not melt and remain approximately unaltered.

Alternative materials can also be used for the integrated liner other than PEBA, such as PTFE, that will melt and integrate with the outer tube melted around the outside of the catheter, which can also be made of other materials. A mandrel may still be inserted within the interior, integrated liner prior to integration to ensure that the interior lumen walls are as smooth as possible, so as to prevent an embolic coil from catching on any deformation on the interior of the catheter as the coil is pushed along the interior length of the catheter. As a result of the physical transformation of the outer tube or inner liner as a result of being integrated, the final product does not include either an outer tube or an inner liner, but rather a fully integrated skin or matrix around the skeletal structure of the guidewire or catheter. When a mandrel is used to form the lumen, the mandrel is pulled from the tube after the matrix has been melted and formed around the skeleton, leaving the lumen. The mandrel would be coated with a material that does no integrate with the skeleton and enables the mandrel to be readily removed.

Those skilled in the art will recognize that there are myriad permutations of resultant beam width, x-axis distance between resultant beams, stock materials, and laminate materials that can be combined to produce laminated guidewires and catheters of various flexibilities and strengths. This specification intends to cover all such permutations of a micro-cut skeletal guidewire/catheter substructure with an integrated flexible matrix, which may also be referred to as a reinforced skeleton or substructure. For example, it is possible to combine a stock material and a laminate material that are much closer in properties (stiffness and/or melting temperature, for example). Materials with significantly closer properties may interact more during the melting phase—with stock material crossing the theoretical boundary between where the ring and resultant beam substructure ends and where the laminate layer begins, and vice versa—resulting in a guidewire/catheter with advantageous flexing and torquing properties. In another example, it is possible to utilize more than one layer of laminate, and each layer may be formed of a different material with differing properties.

The herein disclosed laminated micro-cut guidewire/catheter can in fact be thought of as essentially a highly flexible catheter with a rigid substructure or skeleton to facilitate torque transmission—an entirely new product vastly different than currently available micro-cut catheters and guidewires. An additional benefit to the laminating technique is that the laminate material serves to encapsulate some or the entire micro-cut outer surface of the guidewire or catheter and thus smoothing any burrs, and trapping any debris, that may have formed during the micro-cutting process. This is an additional protection for the patient against any foreign material that may otherwise be released into the body.

A further embodiment of the micro-cut skeletal guidewire/catheter substructure with an integrated elastomeric matrix involves the creation of a shape holding tip, as also initially described above. The shape holding tip product is generated by producing a skeleton for a product and placing the product in a mold or shaped mandrel that holds the tip of the product in a particular position, such as with a slightly curved distal tip. The skeleton is then filled with PEBA to fill in the cuts, but as the cuts are filled, the cuts on the inside of the curved tip will be filled with less PEBA than the cuts on the outside of the curved tip, causing the curved tip to hold its shape once the PEBA has set.

Another embodiment includes a stainless steel hypotube proximal portion that is wrapped around its exterior with a polyethylene shrink tubing that extends beyond the distal end of the hypotube or even beyond the distal end of the machined portion (the very tip of the device). When the shrink tubing is heated or re-melted, it will shrink to form a tight seal or bond around the hypotube, but will only shrink so far at the distal end, leaving a shrink tube catheter at the distal end with a smaller diameter and possibly with a much more flexible tip. An alternative embodiment involves running a micro-cut catheter through a portion of or the entire length of the hypotube and extending beyond the distal end of the hypotube, around which the shrink tube can form. The distal portion of this embodiment would have a smaller outer diameter than the outer diameter of the hypotube so that the catheter tapers toward the distal end.

These different types of microfabricated distal sections (MDS) have a number of advantages: they are kink resistant and do not ovalize, which prevents coils from jamming inside the catheter's distal end; they allow for increased torque transmission and operator control of the distal tip; they allow for increasing the diameter while maintaining superior flexibility; they allow for greater tip stability during delivery of detachable coils or other embolic materials; and they allow for paintbrushing without prolapsed of the distal tip. Paintbrushing refers to the side to side motion of the distal tip, which is necessary for certain operations, such as the more precise placement of detachable coils into desired locations. The ability to paintbrush may also allow for more compact and complete occlusion of vascular anomalies, such as intracranial aneurysms. It may also allow for placing one or two additional coils than might otherwise be possible with prior art devices because the operator can manipulate the distal tip to place it in an area of the aneurysm that still requires filing.

An alternative embodiment involves attaching a micro-cut catheter to the end of the hypotube that has a larger outer diameter than the hypotube and shrinking shrink tubing around both the proximal and distal portions to help hold the distal portion in place and provide fluid integrity. If not clear from above, the shrink tubing just provides an alternative substance and method for forming the flexible matrix for the same or other skeletal based structures already described. In any of these embodiments, radiopaque markers could be placed near the distal tip of the catheter.

Other embodiments involve assembling a skeletal structure catheters from a number of different micro-cut tubes of different durometers and varying lumen wall thicknesses, and either cutting each of tubes according to the same pattern, or varying the pattern for the different tubes. For example, over some sections of the catheter, the cuts may be made very close to one another, while in other sections, the cuts may be further spaced apart. Likewise, in some sections, the resultant beams may be bigger than in other sections. Numerous different variations to the pattern are possible.

A kink resistant proximal portion can be created by micro-cutting a section of PEEK tubing and laminating that section with PEBA, as described above. This combination will allow the proximal portion to bend without kinking. The stiffness of the proximal portion can also be varied by varying the cut spacing between cuts and the depth of each cut, as well as by varying the durometer of the elastomeric material used in the lamination.

A reinforced substructure catheter of the type described herein also creates new possibilities for utilization. The thin lumen walls of prior art catheters cannot withstand significant pressure from within the lumen without having the lumen collapse or having the lumen walls rupture. As a result, the same highly flexible catheters that are often used to place embolic coils in curvaceous vasculature, such as in the brain, have not be usable to remove blood clots that may also be present within the brain because the blood clots need to be extracted by applying vacuum pressure to the catheter at the proximal end 11. The reinforced substructure catheter embodiment (even with a skeletal structure having an outer diameter as small as 0.005 inches), however, is flexible enough to be able to reach far into the vasculature of the brain, yet strong enough to be able to withstand vacuum pressure applied at the proximal end 11 that is sufficient to enable the extraction of blood clots.

Figure 11:
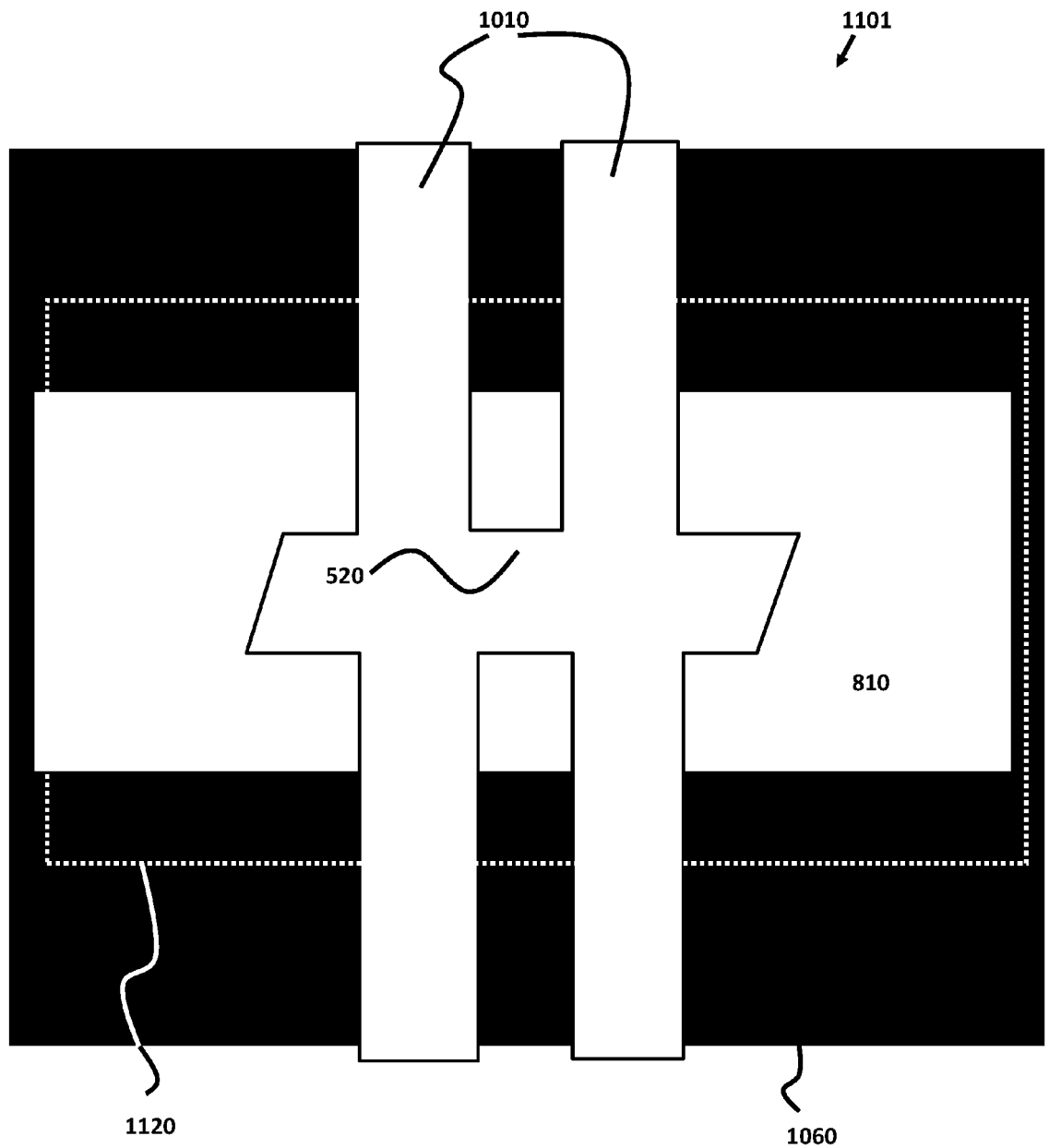
FIG. 11 illustrates an elastomer laminate utilized to restore fluid pressure integrity to a micro-cut catheter in accordance with an embodiment.

As described above, the elastomeric matrix technique can be utilized to forgo the need for a liner tube on the outside or the inside of a micro-cut catheter that has been micro-cut through its lumen walls as described above. FIG. 11 illustrates a method for producing liner-free laminated catheter 1101. In FIG. 11, the dotted line represents original lumen wall 1120 formed by the stock material. As can be inferred from the location and width of resultant beam 520, when the catheter was micro-cut, the pairs of cuts penetrated original lumen wall 1120, producing fenestrations throughout the length of the catheter and destroying the fluid pressure integrity of the lumen. The depth of such fenestrations may be exaggerated by FIG. 11. But this fluid pressure integrity can be re-established during lamination by formation of the elastomeric matrix 1060 within the fenestrations throughout the length of the catheter. The elastomeric matrix 1060 can be formed in a number of different manners, including through the use of shrink tubing or other materials that can be placed on the outside and/or inside of the skeletal structure and melted or otherwise integrated together to form the matrix 1060.

A releasable mandrel coated on its outer surface with TFA, PTFE, or another non-stick layer, so as to facilitate easy removal following the melting stage, could also be inserted into the lumen 810 to help mold the matrix 1060 as it is being formed. The releasable mandrel can be inserted into the lumen 810 after micro-machining the stock material and before pulling a laminate material tube overtop or otherwise creating the outer surface of the matrix 1060. The laminate material is then heated and melted, or otherwise integrated, such as described above, forming laminate matrix/layer 1060. As is apparent in FIG. 11, laminate layer 1060 will fill in the micro-cuts, around rings 1010. After the melting stage, the releasable mandrel (if used) can be removed, resulting in a new lumen wall for the lumen 810. Depending on what type of laminate material is used, it may be necessary to then coat the newly established lumen walls with a hydrophilic coating. For example, if PEBA is used as a laminate material then a hydrophilic coating may be required inside the lumen because PEBA is relatively non-slippery.

Figure 12:
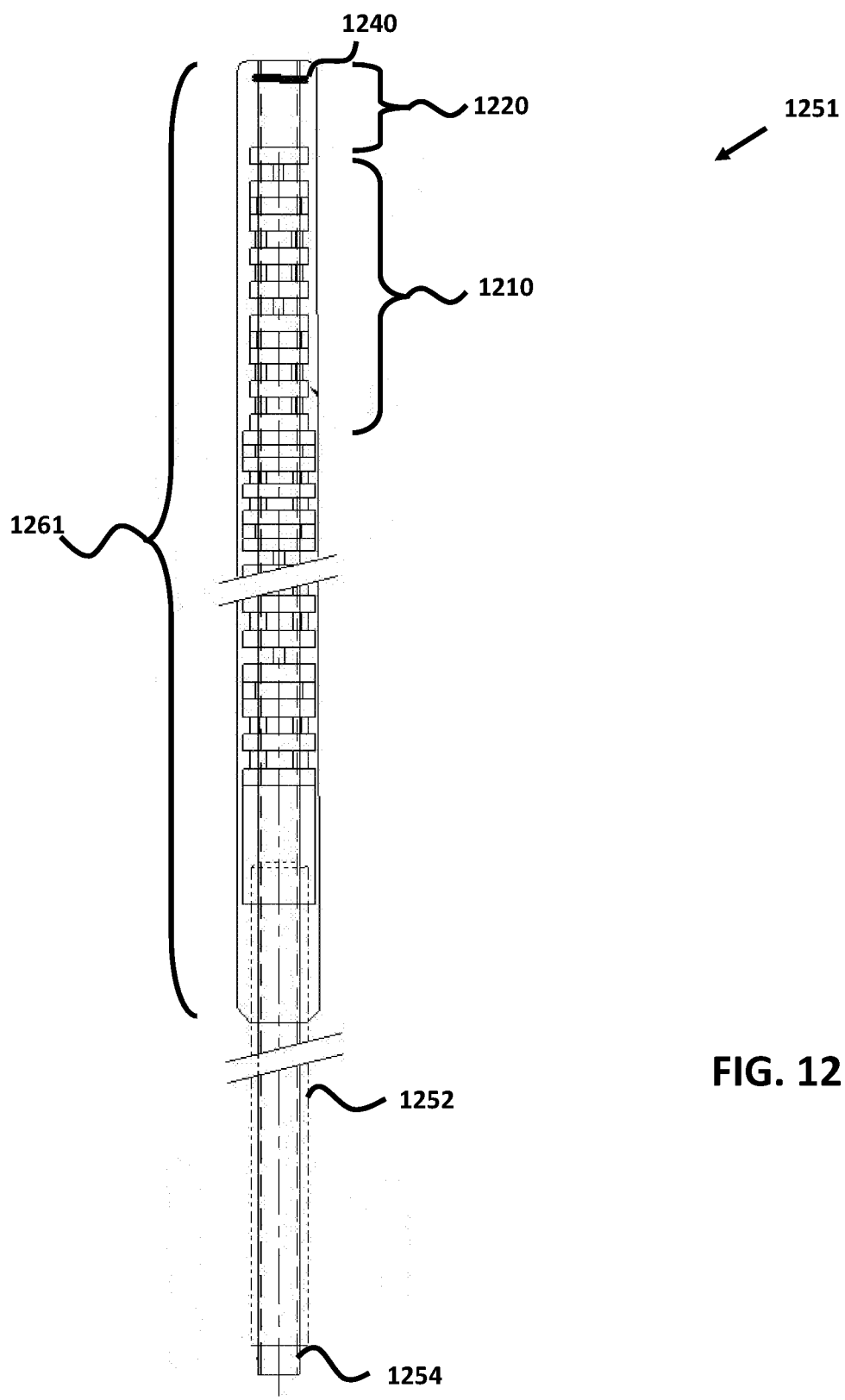
FIG. 12 illustrates a soft tip configuration for a micro-cut catheter in accordance with an embodiment.

As previously described, a soft tip configuration, which may be implemented with any of the above-described catheters and guidewires, will now be described. FIG. 12 illustrates the soft tip configuration as implemented on a hybrid catheter, but it should be noted that the same process can be applied to implement a soft tip configuration on a guidewire. Soft tip hybrid catheter 1251 includes a stainless steel tubing proximal portion 1252, an elastomeric laminated distal section 1261 encasing a micro-cut polymer catheter, and a liner tube 1254 running at least part of the way between the proximal portion and the distal portion. The liner tube 1254 would typically be a slippery material that lacks the strength to retain fluid, but helps to improve the movement of a guidewire or coils through the lumen. The soft tip configuration includes two portions of the catheter: a thinner wall section 1210 and a soft tip section 1220.

The thinner wall section 1210 can be formed in a number of different manners, such by increasing the size of the lumen near the distal end, such as by drilling or otherwise removing some portion of the lumen walls along section 1210. A larger lumen can also be formed by forming the matrix differently along this section 1210, such that the lumen walls are thinner and the lumen is larger, such as using a slightly larger diameter mandrel at the distal end than along other portions of the catheter.

Soft tip section 1220 encompasses the most distal portion of soft tip hybrid catheter 1251, and comprises either the liner tubing 1254 extending beyond the end of the micro-cut polymer catheter section, or an outer covering extending beyond the end of the section. This soft tip section 1220 can be wrapped with relatively thin gauge radiopaque wire 1240 (having a diameter of approximately 0.002 to approximately 0.003 inches), both to provide x-ray visibility while inside the patient's vasculature and to facilitate the taking of a set, or a bend, fixed by the surgeon prior to a procedure. The radiopaque wire 1240 can be coiled relatively tightly around soft tip section 1220 in order to slightly stiffen the soft tip configuration and to robustly hold the surgeon's custom bend, or the radiopaque wire 1240 can be coiled more loosely in order to soften the soft tip configuration and to more loosely hold the surgeon's custom bend.

The soft tip configuration is advantageous for several reasons. The configuration smoothly transmits torque from torquer 12 (not shown in FIG. 12), through proximal portion 14 (stainless steel tubing 1252 as illustrated in FIG. 12) and the micro-machined polymer section to the most distal portion of the catheter, soft tip section 1220. The configuration also provides a gradual stiffness transition from the micro-cut section through the reduced outer diameter section to the soft tip section. Finally, as described above the radiopaque wrapped soft tip section 1220 can take and hold a set, allowing the surgeon to individually optimize the shape of the tip for a particular application or procedure.

The soft tip configuration can be utilized to produce a soft tip guiding catheter that has a larger internal diameter without increasing the external diameter of the catheter. Guiding catheters are typically of a large diameter, having a relatively large diameter lumen, so as to facilitate pumping large volumes of fluid, such as radiopaque dyes or liquid medications, to particular locations within a patient's vasculature. The typical large diameter, however, makes these guiding catheters much more rigid than smaller diameter catheters or micro-catheters. But as explained above, the dual-blade micro-cutting machine allows micro-cutting of polymer stock material— allowing large diameter lumen-forming polymer stock material to be micro-machined into more flexible catheters. This is especially advantageous for traveling through a patient's carotid siphon, a portion of the human vasculature than is especially curvaceous. Previously, it was impossible to produce a large diameter polymer guiding catheter of sufficient flexibility (while retaining torque transmission capabilities) to travel through the carotid siphon, but the dual-blade micro-cutting machine described herein is capable of micro-cutting lumen-forming polymer stock material to the appropriate flexibility. In an embodiment, this guiding catheter is a two piece catheter micro-cut from large diameter polymer stock material with a soft tip configuration as described above at its distal end.

For certain types of surgical procedures, it is desirable to use a flexible guiding catheter to reach a particular point, and to then use a smaller catheter or guidewire inserted inside the larger guiding catheter to reach further points in the body. For example, a guiding catheter of the type described above could be used to reach and extend around the curve of the carotid siphon, and once that has been achieved, to use the smaller catheter or guidewire to reach other vascular in the brain. Under such circumstances, it is also desirable to be able to push contrast solution or other fluids in the lumen gap, which is the gap defined by the difference between the lumen walls and the outside of the inserted catheter, such as a microcatheter. The walls of the lumen are said to define the outer diameter of the lumen gap, while the outer diameter of the microcatheter is said to define the inner diameter of the lumen gap. Hence, if a guiding catheter has an inner diameter of 0.056 inches and the microcatheter has an outer diameter of 0.039 inches, there is 0.017 inches worth of space left to form the lumen gap, which is on either side of the microcatheter, so essentially leaving 0.0085 inches on either side of the microcatheter through which to push fluid. This small lumen gap can require a surgeon to exert some significant force in order to push the fluid all of the way along the length of the guiding catheter.

It has been known in the prior art to taper the outer diameter of the distal end of a microcatheter because the flexibility of a catheter (or guidewire) increases by the fourth power of the outer diameter of the product, and high flexibility at the distal tip is important in many applications. For example, the diameter of a prior art microcatheter may go from 0.039 inches at the proximal portion, where fluid is being pushed by, to an diameter of 0.028 inches or 0.030 inches at the distal tip, which has passed beyond the guiding catheter and is now in the open vasculature. The problem with this design is that the microcatheter is actually bigger where it needs to be small and smaller where it could use to be a little larger.

A embodiment of the micro-cut catheter described herein solves this problem by actually reducing the diameter of the inserted catheter along the length of the proximal portion that is within the guiding catheter so that is easier for a surgeon to push fluid through the lumen gap. Using the same example as above, by reducing the diameter of the inserted catheter along the proximal section from about 0.039 inches to about 0.030 inches, the lumen gap is increased by more than about 50%. At the same time, because of the enhanced flexibility of herein described micro-cut products, the diameter of the microcatheter at the distal end can be increased to about 0.039 inches, giving the surgeon great control and torqueability where it is needed the most. This is only possible due to the highly flexible design of the micro-cut material used for the distal portion and/or the distal tip of the catheter, such as PEEK, which has all of the flexibility of a much small prior art distal tip formed of other materials.

Generally, the modulus of elasticity of the material used to form the skeletal structure of an integrated matrix product can be less than approximately 19 MPa. As the modulus of the material used increase, the beam size can decrease, further enhancing flexibility, but introducing the potential for breakage when the material is stressed beyond a breakage point for the material. The introduction of the integrated matrix actually serves to provide a more linear deformation range for the product because it provides support for the skeleton without impeding flexibility. If a higher modulus is desired, the polymer (plastic) material used as stock material for each of the above described catheters and guidewires can be stiffened (the material's modulus can be increased) by the addition of fibers prior to extrusion. Glass or carbon fibers can be added to the mix of industrial polymer pellets before the pellets are extruded to form the stock material described above. The fiber acts in much the same way as rebar in concrete—including veins of the higher modulus material throughout the polymer increases the overall modulus of the polymer.

Figure 13:
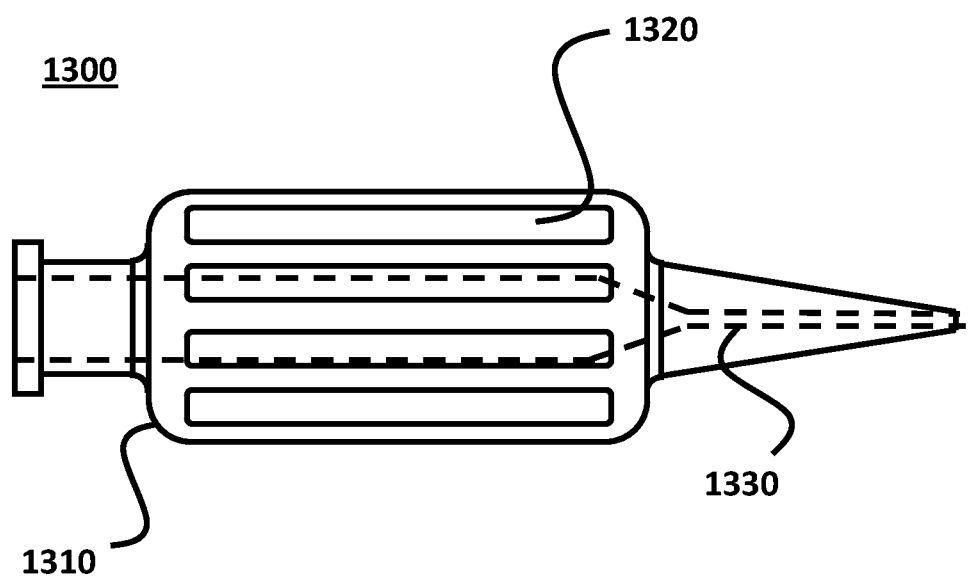
FIG. 13 illustrates a torqueable hub in accordance with an embodiment.
Figure 14A:
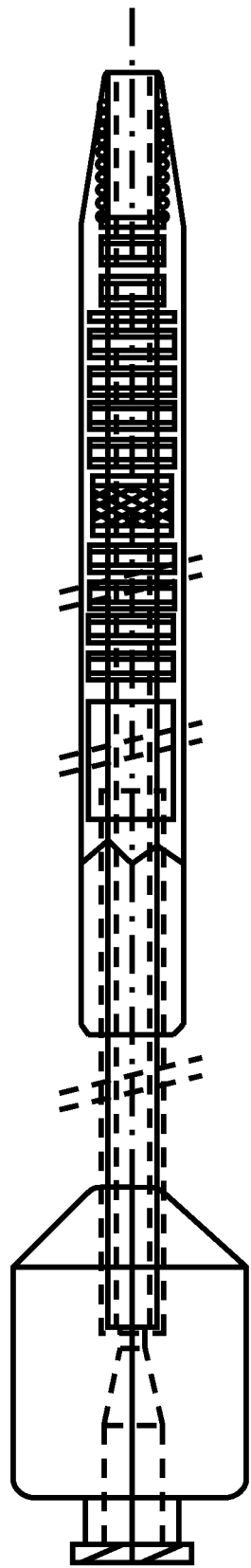
FIG. 14A illustrates a guidewire device in accordance with one or more embodiments.
Figure 15B:
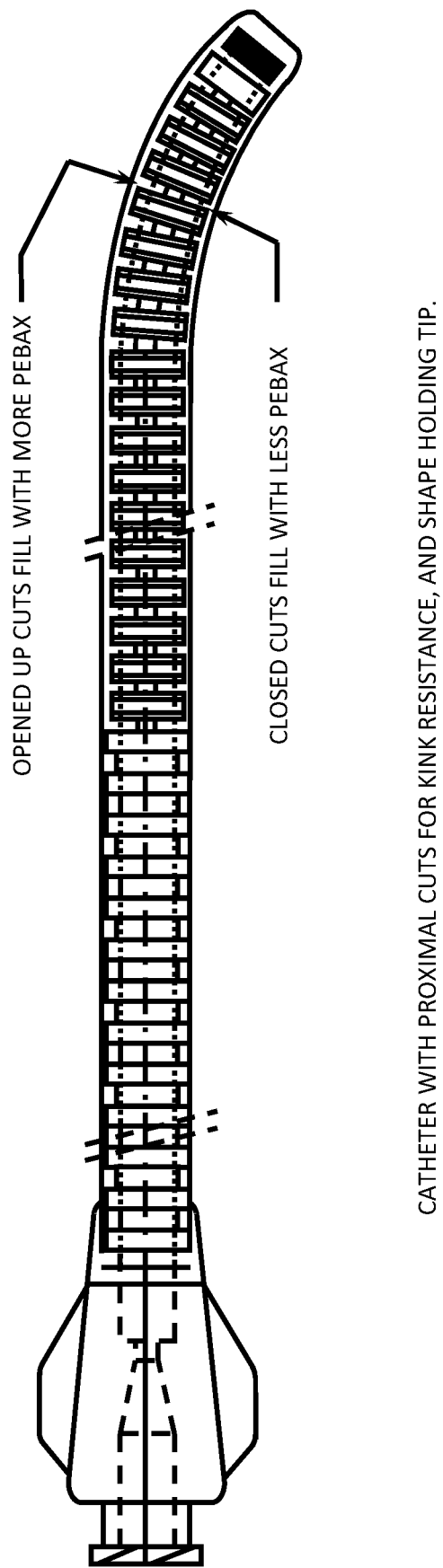
FIG. 15B illustrates a catheter device in accordance with one or more embodiments.

In addition to the advances in products described above, an easier to use and more efficient torqueable hub is also disclosed herein with reference to FIG. 13. Prior art torqueable hubs typically have two large wings or flanges, like certain types of fishing lures that are designed to flutter as water rushes past. The wings or flanges protrude from opposite sides of the hub and are intended to give a surgeon a substantial area to hold and push against when seeking to turn the catheter during an operation. The hub also typically includes an axial space into which a syringe can be inserted so that fluid can be pushed into the catheter. The lure shaped hub, however, is oddly shaped and can be awkward for a surgeon to grip and turn. This shape also impedes the surgeon's ability to exert fine motor skill controls with their fingers, due to the large size of the winged structure.

FIG. 13 illustrates an improved torqueable hub 1300 that has a barrel-shaped body 1310 that includes a plurality of longitudinal grooves 1320 formed in and around the exterior of body 1310. The diameter of the barrel body 1310 is approximately 0.5 inches. The size and shape of the barrel body 1310, coupled with the grooves 1320, give the surgeon a better and more comfortable grip and allow the surgeon to exert much finer control of the torqueable hub 1300, and therefore more accurately control of the catheter. The torqueable hub 1300 also includes an axial interior space, illustrated by the dotted lines 1330, into which a syringe can be inserted.

Many useful and novel devices can be fashioned using micro fabricated elongate members. Such devices are not limited to having just a round cross-section, as is most often seen, but may include other shapes such as oval, square, triangular, or arbitrary, that is, non uniform shapes. These members can be of almost any cross sectional dimension, from very small, such as approximately 0.004", to very large, such as, up to several inches, indeed there is no size limitation as the present embodiments can be scaled according to the desired application. The micro-fabricated detailed structures, referred to herein as "beams" or "resultant beams" and "rings" are fashioned to optimize the performance of the elongate members for their desired purposes. These structures can be formed using a micro-fabrication machine, or by other methods such as laser cutting. For larger structures, what is referred to as "micro-fabrication" may not be necessary, rather more conventional and larger fabrication tools and techniques may be used. In these structures, the general objective of optimizing performance such as torque transmission, flexibility, and push (axial strength) can be achieved just the same as with micro-fabricated structures employing a basic scale up of size.

The following are some of the examples of novel and useful elongate members that can be made using embodiments disclosed herein. These examples are directed to round structures that are of the general size for medical applications, however the embodiments taught herein are readily applicable to other applications where alternate sizes, and shapes are desired.

Examples of structures fabricated with beams, rings, and the like taught herein are as follows:

EXAMPLE 1

A Solid Mono-Filament Stock Material Of Metal Or Polymer, or other material.

EXAMPLE 2

A solid mono-filament stock material that is a composite, for example, co-extruded with various polymer layers, or glass fiber filled or carbon fiber filled materials.

EXAMPLE 3

A solid mono-filament material that may be a polymer that has been coated over a wire such as stainless steel.

EXAMPLE 4

A tubular member made with any of the materials as above, where the interior lumen is not breached by the cutting of features or micro-fabrication.

EXAMPLE 5

A tubular member as in Example 4 where the lumen is breached by the feature cutting.

EXAMPLE 6

Any tubular member such as in Example 5 where there is also a wire disposed in the lumen.

EXAMPLE 7

All of the above Examples 1 to 6, where the cut features (gaps or fenestrations) are substantially filled such that the outer surface is relatively smooth and the adjoining rings of the structures are essentially in mechanical contact with each other through the filling matrix material, such as polyether block amide, also referred to as PEBA or Pebax™, which is of lower modulus than the cut material.

EXAMPLE 8

As in example 7 where the matrix material completely encapsulates the cut material, including interior portions for tubular material forming an interspersed skeleton of stronger material inside a fluid sealed wall of the matrix material.

EXAMPLE 9

As in example 8 where some of the cuts or fenestrations are left open for fluid delivery or other purposes.

EXAMPLE 10

In an example of an elongate member used for catheters or guidewires, the above examples can be fashioned for use by using the member for the entire length, for example, 175 cm in the case of one type of catheter.

EXAMPLE 11

Devices and structures contemplated herein also includes members having multiple lumen, such as, a catheter, guidewire, or the like, having two, three or more lumen.

EXAMPLE 12

Devices and structures contemplated herein also includes members using braiding.

Any of the examples above, could be used in segments together, or with other materials to form various catheters or guidewires or any other structure to form elongate members of various segments along the length. These segments may have a larger or smaller relative cross section and be placed at various locations relative to one another such as at a distal segment or proximal segment in the instances of medical devices. These materials may include solid stainless steel or other material, including a stainless steel wire that is ground to a taper, or a tubular structure of stainless or other material. These adjoining segments may include some micro-fabricated features along all or part of the length. Further, the various segments may use a portion of the adjoining segment, such as, a continuous interiorly disposed member of Example 6, where the wire might continue from one segment to another.

An embodiment of the present invention provides a catheter device comprising: a micro-fabricated elongated outer member having an outer surface and an interior surface forming a lumen extending from a proximal end to a distal end and a plurality of fenestrations made through the outer surface and the interior surface into at least a portion of the lumen; and an outer elastomer laminate layer in contact with at least a portion of the outer surface and filling the plurality of fenestrations.

An aspect of the present embodiment further comprising a torqueable hub connected to the proximal end and having a barrel-shaped body with a plurality of longitudinal grooves formed therein, and further forming an axial interior space within which a syringe can be inserted.

An aspect of the present embodiment is where the micro-fabricated elongated outer member has a plurality of resultant beams, each resultant beam formed between adjacent fenestrations among the plurality of fenestrations.

An aspect of the present embodiment is where the outer elastomer laminate layer substantially covers all of the resultant beams.

An aspect of the present embodiment is where the outer elastomer laminate layer covers completely all of the resultant beams.

An aspect of the present embodiment is where the micro-fabricated elongated outer member forms an interspersed skeleton and wherein the outer elastomer laminate layer forms a matrix of flexible material that is disposed around the interspersed skeleton.

An aspect of the present embodiment is where the micro-fabricated elongated outer member is formed from polyetheretherketone.

An aspect of the present embodiment is where the outer elastomer laminate layer is formed from polyether block amide.

An aspect of the present embodiment further comprising a lubricious liner formed from PTFE in contact with the interior surface.

An aspect of the present embodiment is where the micro-fabricated elongated outer member is formed from a material having a modulus value of about 3700 MPa.

An aspect of the present invention is where the outer elastomer laminate layer is formed from a material having a modulus value of about 12 MPa.

An aspect of the present invention is where the outer elastomer laminate layer extends beyond the distal end to form a hollow distal tip.

An aspect of the present invention is where the hollow distal tip includes a wire holding a shape for the hollow distal tip.

An aspect of the present invention is where the hollow distal tip includes a radiopaque marker.

An embodiment of the present invention provides a guidewire device comprising: a micro-fabricated elongated outer member having an outer surface and an interior surface forming a lumen extending from a proximal end to a distal end and a plurality of fenestrations made through the outer surface and the interior surface into a least a portion of the lumen; an outer elastomer laminate layer in contact with at least a portion of the outer surface and filling at least a portion of the plurality of fenestrations; and an inner member disposed within a substantial portion of the lumen.

An aspect of the present embodiment is where the inner member is a monofilament wire core.

An aspect of the present embodiment is where the inner member is a hypotube.

An aspect of the present embodiment is where the micro-fabricated elongated outer member has a plurality of resultant beams, each resultant beam formed between adjacent fenestrations among the plurality of fenestrations.

An aspect of the present embodiment is where the outer elastomer laminate layer substantially covers all of the resultant beams.

An aspect of the present embodiment is where the outer elastomer laminate layer covers completely all of the resultant beams.

An aspect of the present embodiment is where the micro-fabricated elongated outer member forms an interspersed skeleton and where the outer elastomer laminate layer forms a matrix of flexible material that is disposed around the interspersed skeleton.

An aspect of the present embodiment is where the micro-fabricated elongated outer member is formed from polyetheretherketone.

An aspect of the present embodiment is where the outer elastomer laminate layer is formed from polyether block amide.

An aspect of the present embodiment, further comprising a lubricious liner formed from PTFE in contact with the interior surface.

An aspect of the present embodiment is where the micro-fabricated elongated outer member is formed from a material having a modulus value of about 3700 MPa.

An aspect of the present embodiment is where the outer elastomer laminate layer is formed from a material having a modulus value of about 12 MPa.

An aspect of the present embodiment is where the outer elastomer laminate layer extends beyond the distal end to form a hollow distal tip.

An aspect of the present embodiment is where the hollow distal tip includes a wire holding a shape for the hollow distal tip.

An aspect of the present embodiment is where the hollow distal tip includes a radiopaque marker.

An embodiment of the present invention provides a catheter device comprising: a micro-fabricated elongated outer member having an outer surface and an interior surface forming a lumen extending from a proximal end to a distal end; and an outer elastomer laminate layer in contact with at least a portion of the outer surface.

An aspect of the present embodiment, further comprising a torqueable hub connected to the proximal end and having a barrel-shaped body with a plurality of longitudinal grooves formed therein, and further forming an axial interior space within which a syringe can be inserted.

An aspect of the present embodiment is where the micro-fabricated elongated outer member has a plurality of resultant beams, each resultant beam formed between adjacent rings among the plurality of rings.

An aspect of the present embodiment is where the outer elastomer laminate layer substantially covers all of the resultant beams.

An aspect of the present embodiment is where the outer elastomer laminate layer covers completely all of the resultant beams.

An aspect of the present embodiment is where the micro-fabricated elongated outer member forms an interspersed skeleton and wherein the outer elastomer laminate layer forms a matrix of flexible material that is disposed around the interspersed skeleton.

An aspect of the present embodiment is where the micro-fabricated elongated outer member is formed from polyetheretherketone.

An aspect of the present embodiment is where the outer elastomer laminate layer is formed from polyether block amide.

An aspect of the present embodiment, further comprising a lubricious liner formed from PTFE in contact with the interior surface.

An aspect of the present embodiment is where the micro-fabricated elongated outer member is formed from a material having a modulus value of about 3700 MPa.

An aspect of the present embodiment is where the outer elastomer laminate layer is formed from a material having a modulus value of about 12 MPa.

An aspect of the present embodiment is where the outer elastomer laminate layer extends beyond the distal end to form a hollow distal tip.

An aspect of the present embodiment is where the hollow distal tip includes a wire holding a shape for the hollow distal tip.

An aspect of the present embodiment is where the hollow distal tip includes a radiopaque marker.

An embodiment of the present invention provides a guidewire device comprising: a micro-fabricated elongated outer member having an outer surface and an interior surface forming a lumen extending from a proximal end to a distal end; an outer elastomer laminate layer in contact with at least a portion of the outer surface; and an inner member disposed within a substantial portion of the lumen.

An aspect of the present embodiment is where the inner member is a monofilament wire core.

An aspect of the present embodiment is where the inner member is a hypotube.

An aspect of the present embodiment is where the micro-fabricated elongated outer member has a plurality of resultant beams, each resultant beam formed between adjacent rings among a plurality of rings.

An aspect of the present embodiment is where the outer elastomer laminate layer substantially covers all of the resultant beams.

An aspect of the present embodiment is where the outer elastomer laminate layer covers completely all of the resultant beams.

An aspect of the present embodiment is where the micro-fabricated elongated outer member is formed from nitinol.

An aspect of the present embodiment is where the outer elastomer laminate layer is formed from polyether block amide.

An aspect of the present embodiment is where the micro-fabricated elongated outer member is formed from a material having a modulus value of about 3700 MPa.

An aspect of the present embodiment is where the outer elastomer laminate layer is formed from a material having a modulus value of about 12 MPa.

An aspect of the present embodiment is where the outer elastomer laminate layer extends beyond the distal end to form a hollow distal tip.

An aspect of the present embodiment is where the hollow distal tip includes a wire holding a shape for the hollow distal tip.

An aspect of the present embodiment is where the hollow distal tip includes a radiopaque marker.

An embodiment of the present invention provides a guidewire device comprising a solid material micro-fabricated elongated outer member having a plurality of resultant beams, each resultant beam formed between adjacent rings among a plurality of rings.

An aspect of the present embodiment is where the micro-fabricated elongated outer member is formed from nitinol.

An aspect of the present embodiment, further comprising an outer elastomer laminate layer covering at least a portion of the resultant beams.

An aspect of the present embodiment is where the outer elastomer laminate layer is formed from polyether block amide.

An aspect of the present embodiment is where the outer elastomer laminate layer is formed from a material having a modulus value of about 12 MPa.

An embodiment of the present invention provides a catheter device comprising: a micro-fabricated elongated outer member having an outer surface and an interior surface forming a lumen extending from a proximal end to a distal end, wherein the outer member is formed from two or more different stock materials.

An aspect of the present embodiment, further comprising a torqueable hub connected to the proximal end and having a barrel-shaped body with a plurality of longitudinal groves formed therein, and further forming an axial interior space within which a syringe can be inserted.

An aspect of the present embodiment is where a first stock material of the two or more different stock materials is stainless steel.

An aspect of the present embodiment is where the stainless steel is used at the proximal end.

An aspect of the present embodiment is where a second stock material of the two or more different stock materials is nitinol.

An aspect of the present embodiment is where the nitinol is used at the proximal end.

An aspect of the present embodiment, further comprising an outer elastomer laminate layer in contact with at least a portion of the outer surface.

An aspect of the present embodiment is where the micro-fabricated elongated outer member forms an interspersed skeleton and wherein the outer elastomer laminate layer forms a matrix of flexible material that is disposed around the interspersed skeleton.

An aspect of the present embodiment is where the outer elastomer laminate layer extends beyond the distal end to form a hollow distal tip.

An aspect of the present embodiment is where the hollow distal tip includes a wire holding a shape for the hollow distal tip.

An aspect of the present embodiment is where the hollow distal tip includes a radiopaque marker.

An aspect of the present embodiment is where the micro-fabricated elongated outer member further forms a plurality of fenestrations made through the outer surface and the interior surface into at least a portion of the lumen; and further comprising an outer elastomer laminate layer in contact with at least a portion of the outer surface and filling the plurality of fenestrations.

An aspect of the present embodiment is where the micro-fabricated elongated outer member forms an interspersed skeleton and wherein the outer elastomer laminate layer forms a matrix of flexible material that is disposed around the interspersed skeleton.

An aspect of the present embodiment is where the micro-fabricated elongated outer member further forms a plurality of fenestrations made at a distal portion of the outer member, and through the outer surface and the interior surface into at least a portion of the lumen; and further comprising an outer elastomer laminate layer in contact with at least a portion of the outer surface and filling the plurality of fenestrations.

An aspect of the present embodiment is where the micro-fabricated elongated outer member further forms a plurality of fenestrations made at a proximal portion of the outer member, and through the outer surface and the interior surface into at least a portion of the lumen; and further comprising an outer elastomer laminate layer in contact with at least a portion of the outer surface and filling the plurality of fenestrations.

An aspect of the present embodiment is where the micro-fabricated elongated outer member has an outer diameter of the distal end that is larger than an outer diameter of the proximal end.

An embodiment of the present invention provides a guidewire device comprising: a micro-fabricated elongated outer member having an outer surface and an interior surface forming a lumen extending from a proximal end to a distal end, wherein the outer member is formed from two or more stock materials; and an inner member disposed within a portion of the lumen.

An aspect of the present embodiment is where the inner member is a monofilament wire core.

An aspect of the present embodiment is where the inner member is a hypotube.

An aspect of the present embodiment is where a first stock material of the two or more different stock materials is stainless steel.

An aspect of the present embodiment is where the stainless steel is used at the proximal end.

An aspect of the present embodiment is where a second stock material of the two or more different stock materials is nitinol.

An aspect of the present embodiment is where the nitinol is used at the distal end.

An aspect of the present embodiment, further comprising an outer elastomer laminate layer in contact with at least a portion of the outer surface.

An aspect of the present embodiment is where the micro-fabricated elongated outer member further forms a plurality of fenestrations made through the outer surface and the interior surface into at least a portion of the lumen; and further comprising an outer elastomer laminate layer in contact with at least a portion of the outer surface and filling the plurality of fenestrations.

An aspect of the present embodiment is where the micro-fabricated elongated outer member forms an interspersed skeleton and wherein the outer elastomer laminate layer forms a matrix of flexible material that is disposed around the interspersed skeleton.

An aspect of the present embodiment is where the micro-fabricated elongated outer member further forms a plurality of fenestrations made at a distal portion of the outer member, and through the outer surface and the interior surface into at least a portion of the lumen; and further comprising an outer elastomer laminate layer in contact with at least a portion of the outer surface and filling the plurality of fenestrations.

An aspect of the present embodiment is where the micro-fabricated elongated outer member further comprises a plurality of fenestrations made at a proximal portion of the outer member, and through the outer surface and the interior surface into at least a portion of the lumen; and further comprising an outer elastomer laminate layer in contact with at least a portion of the outer surface and filling the plurality of fenestrations.

An aspect of the present embodiment is where the micro-fabricated elongated outer member has an outer diameter of the distal end that is larger than an outer diameter of the proximal end.

An embodiment of the present invention provides a catheter device comprising: an elongated outer member having an outer surface and an interior surface forming a lumen extending from a proximal end to a distal end, wherein an outer diameter of the distal end is larger than an outer diameter of the proximal end.

An aspect of the present embodiment is where the elongated outer member is micro fabricated.

An aspect of the present embodiment is where the elongated outer member is micro-fabricated at the distal portion.

An aspect of the present embodiment, further comprising an inner member formed of a monofilament wire core, the inner member disposed within a portion of the lumen.

An aspect of the present embodiment, further comprising an inner member formed of a hypotube, the inner member disposed within a portion of the lumen.

An aspect of the present embodiment, further comprising a torqueable hub connected to the proximal end and having a barrel-shaped body with a plurality of longitudinal groves formed therein, and further forming an axial interior space within which a syringe can be inserted.

An aspect of the present embodiment is where the outer diameter of the proximal end is about 0.030 inches.

An aspect of the present embodiment is where the outer diameter of the distal end is about 0.039 inches.

An aspect of the present embodiment is where the outer diameter of the proximal end is about 0.030 inches, and the outer diameter of the distal end is about 0.039 inches.

An aspect of the present embodiment is where the lumen has an inner diameter of about 0.024 inches.

An embodiment of the present invention provides a guidewire device comprising: an elongated outer member having an outer surface and an interior surface forming a lumen extending from a proximal end to a distal end, wherein an outer diameter of the distal end is larger than an outer diameter of the proximal end; and an inner member disposed within a portion of the lumen.

An aspect of the present embodiment is where at least a portion of the elongated outer member is micro fabricated.

An aspect of the present embodiment is where the elongated outer member is micro-fabricated at the distal portion.

An aspect of the present embodiment is where the inner member is a monofilament wire core.

An aspect of the present embodiment is where the inner member is a hypotube.

An aspect of the present embodiment, further comprising a torqueable hub connected to the proximal end and having a barrel-shaped body with a plurality of longitudinal groves formed therein, and further forming an axial interior space within which a syringe can be inserted.

An aspect of the present embodiment is where the outer diameter of the proximal end is about 0.030 inches.

An aspect of the present embodiment is where the outer diameter of the distal end is about 0.039 inches.

An aspect of the present embodiment is where the outer diameter of the proximal end is about 0.030 inches, and the outer diameter of the distal end is about 0.039 inches.

An aspect of the present embodiment is where the lumen has an inner diameter of about 0.024 inches.

While embodiments have been illustrated and described herein, it is to be understood that the techniques described herein can have a multitude of additional uses and applications. Accordingly, the invention should not be limited to just the particular description and various drawing figures contained in this specification that merely illustrate one or more embodiments and application of the principles of the invention.

What is claimed is:

1. A guidewire device comprising:
    a micro-fabricated elongated outer member having
        an outer surface and an interior surface forming a lumen extending from a proximal end to a distal end of said micro-fabricated elongated outer member along a longitudinal axis of said micro-fabricated elongated outer member, and
        a plurality of resultant beams formed between adjacent fenestrations made through said outer surface and said interior surface into said lumen, said resultant beams having an outer surface, an inner surface, a proximal surface, and a distal surface, said resultant beams extending spirally around the longitudinal axis such that a flexing bias in said micro-fabricated elongated outer member is reduced, adjacent fenestrations spaced apart along the longitudinal axis of said elongated outer member having between a five degree variance and a forty degree variance;
    a material monolithically encapsulating said elongated outer member, forming an outer elastomer laminate layer, covering said outer surface, said inner surface, said proximal surface, and said distal surface of each resultant beam of said plurality of resultant beams, and completely filling each fenestration of said plurality of fenestrations, said material forming a continuous elastomer lumen at least partially extending along a longitudinal axis of said elongated outer member from said proximal end to said distal end of said elongated outer member; and
    an inner member disposed within a substantial portion of said lumen.

2. The guidewire device of claim 1, wherein said inner member is a monofilament wire core.

3. The guidewire device of claim 1, wherein said inner member is a hypotube.

4. The guidewire device of claim 1, wherein said micro-fabricated elongated outer member is formed from polyetheretherketone.

5. The guidewire device of claim 1, wherein said outer elastomer laminate layer is formed from polyether block amide.

6. The guidewire device of claim 1, further comprising a lubricious liner formed from PTFE in contact with the interior surface.

7. The guidewire device of claim 1, wherein said micro-fabricated elongated outer member is formed from a material having a modulus value of about 3700 MPa.

8. The guidewire device of claim 7, wherein said outer elastomer laminate layer is formed from a material having a modulus value of about 12 MPa.

9. The guidewire device of claim 1, wherein said outer elastomer laminate layer extends beyond said distal end to form a hollow distal tip.

10. The guidewire device of claim 9, wherein said hollow distal tip includes a wire holding a shape for the hollow distal tip.

11. The guidewire device of claim 9, wherein said hollow distal tip includes a radiopaque marker.

12. The guidewire device of claim 1, wherein said proximal end is a hypotube.

13. The guidewire device of claim 1, wherein said outer elastomer layer has a modulus of elasticity less than a modulus of elasticity of said micro-fabricated elongated outer member.

14. The guidewire of claim 1, further comprising a space between said inner member and said interior surface of said lumen.

15. The guidewire of claim 14, wherein said outer elastomer laminate layer fills said space between said inner member and said interior surface of said lumen.

16. The guidewire of claim 1, wherein a distance between said distal end and said proximal end of said micro-fabricated elongated outer member is in the range of approximately 157 cm to 195 cm.

17. The guidewire of claim 1, wherein said fenestrations and said plurality of resultant beams formed by adjacent fenestrations are located along an entire length of said microfabricated elongated outer member.

* * * * *